US012257450B2

(12) United States Patent
Karavitis et al.

(10) Patent No.: US 12,257,450 B2
(45) Date of Patent: *Mar. 25, 2025

(54) DERMATOLOGICAL SYSTEMS AND METHODS WITH HANDPIECE FOR COAXIAL PULSE DELIVERY AND TEMPERATURE SENSING

(71) Applicant: Cutera, Inc., Brisbane, CA (US)

(72) Inventors: Michael A. Karavitis, San Pedro, CA (US); Wytze E. van der Veer, Bennekom (NL); Amogh Kothare, Fremont, CA (US); Soenke A. Moeller, Berkeley, CA (US); Shawn M. Gilliam, Daly City, CA (US)

(73) Assignee: Cutera, Inc., Brisbane, CA (US)

( * ) Notice: Subject to any disclaimer, the term of this patent is extended or adjusted under 35 U.S.C. 154(b) by 223 days.

This patent is subject to a terminal disclaimer.

(21) Appl. No.: 17/676,215

(22) Filed: Feb. 20, 2022

(65) Prior Publication Data
US 2022/0168590 A1 Jun. 2, 2022

Related U.S. Application Data

(63) Continuation of application No. 17/120,237, filed on Dec. 13, 2020, now Pat. No. 11,253,720, which is a
(Continued)

(51) Int. Cl.
*A61N 5/06* (2006.01)
*A61B 17/00* (2006.01)
(Continued)

(52) U.S. Cl.
CPC ......... *A61N 5/0616* (2013.01); *A61N 5/0625* (2013.01); *A61B 2017/00061* (2013.01);
(Continued)

(58) Field of Classification Search
None
See application file for complete search history.

(56) References Cited

U.S. PATENT DOCUMENTS

| 5,098,427 A | 3/1992 | Hessel et al. |
| 5,520,679 A | 5/1996 | Lin |

(Continued)

FOREIGN PATENT DOCUMENTS

| WO | 1999049937 A1 | 10/1999 |
| WO | 2007127924 A2 | 11/2007 |

(Continued)

OTHER PUBLICATIONS

Anderson, Rox R. et al., "Selective Photothermolysis of Lipid-Rich Tissues: A Free Electron Laser Study," Lasers in Surgery & Medicine 38:913-919 (2006), Wiley Interscience.
(Continued)

*Primary Examiner* — Lynsey C Eiseman
(74) *Attorney, Agent, or Firm* — McCarter & English, LLP

(57) ABSTRACT

Dermatological systems and methods for providing a therapeutic laser treatment using a handpiece delivering one or more therapeutic laser pulses to a target skin area along a first optical path, and sensing the temperature of the target skin area based on infrared energy radiating from the target skin area along a second optical path generally counterdirectional to the first optical path, and sharing a common optical axis with the first optical path for at least a portion of the first and second optical paths. The handpiece may also provide contact cooling for a first skin area comprising the target skin area.

12 Claims, 16 Drawing Sheets

Related U.S. Application Data continuation-in-part of application No. 16/805,761, filed on Feb. 29, 2020, now Pat. No. 10,864,380.

(51) Int. Cl.
  *A61B 18/00* (2006.01)
  *A61B 18/20* (2006.01)
  *A61N 5/00* (2006.01)
  *A61N 5/067* (2006.01)

(52) U.S. Cl.
  CPC .......... *A61B 2017/0019* (2013.01); *A61B 2018/00791* (2013.01); *A61B 2018/202* (2013.01); *A61B 2018/20359* (2017.05); *A61N 2005/007* (2013.01); *A61N 2005/0628* (2013.01); *A61N 5/067* (2021.08)

(56) References Cited

U.S. PATENT DOCUMENTS

| | | |
|---|---|---|
| 5,662,643 A | 9/1997 | Kung et al. |
| 5,769,847 A | 6/1998 | Panescu et al. |
| 5,782,822 A | 7/1998 | Telfair et al. |
| 5,976,123 A | 11/1999 | Baumgardner et al. |
| 5,979,454 A | 11/1999 | Anvari et al. |
| 6,015,404 A | 1/2000 | Altshuler et al. |
| 6,026,816 A | 2/2000 | McMillan et al. |
| 6,142,939 A | 11/2000 | Eppstein et al. |
| 6,200,308 B1 | 3/2001 | Pope et al. |
| 6,210,426 B1 | 4/2001 | Cho et al. |
| 6,235,016 B1 | 5/2001 | Stewart |
| 6,328,733 B1 | 12/2001 | Trost |
| 6,408,212 B1 | 6/2002 | Neev |
| 6,451,010 B1 | 9/2002 | Angeley |
| 6,488,696 B1 | 12/2002 | Cho et al. |
| 6,508,813 B1 | 1/2003 | Altshuler |
| 6,514,244 B2 | 2/2003 | Pope et al. |
| 6,517,532 B1 | 2/2003 | Altshuler et al. |
| 6,527,797 B1 | 3/2003 | Masotti et al. |
| 6,605,080 B1 | 8/2003 | Altshuler et al. |
| 6,632,219 B1 | 10/2003 | Baranov et al. |
| 6,638,272 B2 | 10/2003 | Cho et al. |
| 6,663,620 B2 | 12/2003 | Altshuler et al. |
| 6,692,517 B2 | 2/2004 | Cho et al. |
| 6,702,838 B1 | 3/2004 | Andersen et al. |
| 6,723,090 B2 | 4/2004 | Altshuler et al. |
| 6,743,222 B2 | 6/2004 | Durkin et al. |
| 6,758,845 B1 | 7/2004 | Weckwerth et al. |
| 6,770,069 B1 | 8/2004 | Hobart et al. |
| 6,835,202 B2 | 12/2004 | Harth et al. |
| 6,887,233 B2 | 5/2005 | Angeley et al. |
| D507,654 S | 7/2005 | Gollnick et al. |
| 6,951,558 B2 | 10/2005 | Angeley et al. |
| 6,976,985 B2 | 12/2005 | Altshuler et al. |
| 6,991,644 B2 | 1/2006 | Spooner et al. |
| 6,997,923 B2 | 2/2006 | Anderson et al. |
| 7,018,396 B2 | 3/2006 | Sierra et al. |
| 7,044,959 B2 | 3/2006 | Anderson et al. |
| 7,041,094 B2 | 5/2006 | Connors et al. |
| 7,060,061 B2 | 6/2006 | Altshuler et al. |
| 7,184,614 B2 | 2/2007 | Slatkine |
| 7,198,634 B2 | 4/2007 | Harth et al. |
| 7,204,832 B2 | 4/2007 | Altshuler et al. |
| 7,208,007 B2 | 4/2007 | Nightingale et al. |
| 7,245,369 B2 | 7/2007 | Wang et al. |
| 7,250,047 B2 | 7/2007 | Anderson et al. |
| 7,291,140 B2 | 11/2007 | MacFarland et al. |
| 7,326,199 B2 | 2/2008 | MacFarland et al. |
| 7,331,953 B2 | 2/2008 | Manstein et al. |
| 7,351,252 B2 | 4/2008 | Altshuler et al. |
| 7,367,341 B2 | 5/2008 | Anderson et al. |
| RE40,403 E | 6/2008 | Cho et al. |
| 7,427,289 B2 | 9/2008 | Sierra et al. |
| 7,438,713 B2 | 10/2008 | Angeley et al. |
| 7,465,307 B2 | 12/2008 | Connors et al. |
| 7,470,270 B2 | 12/2008 | Azar et al. |
| 7,524,328 B2 | 4/2009 | Connors et al. |
| 7,618,414 B2 | 11/2009 | Connors et al. |
| 7,671,327 B2 | 3/2010 | Clancy et al. |
| 7,703,458 B2 | 4/2010 | Levernier et al. |
| 7,722,600 B2 | 5/2010 | Connors et al. |
| 7,731,953 B2 | 6/2010 | Leonard et al. |
| 7,762,964 B2 | 7/2010 | Slatkine |
| 7,762,965 B2 | 7/2010 | Slatkine |
| 7,763,016 B2 | 7/2010 | Altshuler et al. |
| 7,771,374 B2 | 8/2010 | Slatkine |
| 7,780,652 B2 | 8/2010 | MacFarland et al. |
| 7,814,915 B2 | 10/2010 | Davenport et al. |
| 7,824,396 B2 | 11/2010 | Angeley et al. |
| 7,878,206 B2 | 2/2011 | Connors et al. |
| 7,891,362 B2 | 2/2011 | Domankevitz et al. |
| 7,942,153 B2 | 5/2011 | Manstein et al. |
| 7,975,702 B2 | 7/2011 | Cho et al. |
| D643,530 S | 8/2011 | Ramstad et al. |
| 7,998,181 B2 | 8/2011 | Nightingale et al. |
| 8,002,768 B1 | 8/2011 | Altshuler et al. |
| 8,113,209 B2 | 2/2012 | Masotti et al. |
| 8,172,835 B2 | 5/2012 | Leyh et al. |
| 8,182,473 B2 | 5/2012 | Altshuler et al. |
| 8,190,243 B2 | 5/2012 | Welches et al. |
| 8,211,097 B2 | 7/2012 | Leyh |
| 8,216,215 B2 | 7/2012 | Flyash et al. |
| 8,244,369 B2 | 8/2012 | Kreindel |
| 8,276,592 B2 | 10/2012 | Davenport et al. |
| 8,285,390 B2 | 10/2012 | Levinson et al. |
| 8,317,779 B2 | 11/2012 | Mirkov et al. |
| 8,317,780 B2 | 11/2012 | Davenport et al. |
| 8,322,348 B2 | 12/2012 | Mirkov et al. |
| 8,328,796 B2 | 12/2012 | Altshuler et al. |
| 8,353,899 B1 | 1/2013 | Wells et al. |
| 8,366,703 B2 | 2/2013 | Davenport et al. |
| 8,439,901 B2 | 5/2013 | Davenport et al. |
| 8,454,591 B2 | 6/2013 | Leyh et al. |
| 8,460,280 B2 | 6/2013 | Davenport et al. |
| 8,474,463 B2 | 7/2013 | Levernier et al. |
| 8,506,506 B2 | 8/2013 | Nebrigic et al. |
| 8,523,927 B2 | 9/2013 | Levinson et al. |
| 8,562,599 B2 | 10/2013 | Leyh |
| 8,585,618 B2 | 11/2013 | Hunziker et al. |
| 8,656,931 B2 | 2/2014 | Davenport et al. |
| 8,702,769 B2 | 4/2014 | Eckhouse et al. |
| 8,702,774 B2 | 4/2014 | Baker et al. |
| 8,728,064 B2 | 5/2014 | Schomacker et al. |
| 8,771,263 B2 | 7/2014 | Epshtein et al. |
| 8,778,003 B2 | 7/2014 | Eckhouse et al. |
| 8,834,547 B2 | 9/2014 | Anderson et al. |
| 8,840,608 B2 | 9/2014 | Anderson et al. |
| 8,870,856 B2 | 10/2014 | Connors et al. |
| 8,876,809 B2 | 11/2014 | Eckhouse et al. |
| 8,876,811 B2 | 11/2014 | Lewinsky et al. |
| 8,882,753 B2 | 11/2014 | Mehta et al. |
| 8,915,906 B2 | 12/2014 | Davenport et al. |
| 8,915,948 B2 | 12/2014 | Altshuler et al. |
| 8,920,409 B2 | 12/2014 | Davenport et al. |
| 8,932,278 B2 | 1/2015 | Tankovich et al. |
| 8,936,593 B2 | 1/2015 | Epshtein et al. |
| 9,078,681 B2 | 7/2015 | Koifman et al. |
| 9,078,683 B2 | 7/2015 | Sabati et al. |
| 9,084,587 B2 | 7/2015 | Eckhouse et al. |
| 9,132,031 B2 | 9/2015 | Levinson et al. |
| 9,149,332 B2 | 10/2015 | Koifman et al. |
| 9,161,802 B2 | 10/2015 | Przybyszewski |
| 9,271,793 B2 | 3/2016 | Eckhouse et al. |
| 9,308,120 B2 | 4/2016 | Anderson et al. |
| 9,333,379 B2 | 5/2016 | Azoulay |
| 9,345,531 B2 | 5/2016 | Furnish et al. |
| D759,236 S | 6/2016 | Preiss et al. |
| 9,358,068 B2 | 6/2016 | Schomacker et al. |
| 9,375,345 B2 | 6/2016 | Levinson et al. |
| 9,486,285 B2 | 11/2016 | Paithankar et al. |
| 9,539,439 B2 | 1/2017 | Jones et al. |
| 9,597,528 B2 | 3/2017 | Schomacker et al. |
| 9,685,753 B2 | 6/2017 | Hellstrom et al. |
| 9,907,612 B2 | 3/2018 | Bradley |

(56) References Cited

U.S. PATENT DOCUMENTS

| | | |
|---|---|---|
| 9,913,688 B1 | 3/2018 | Karavitis |
| 9,949,877 B2 | 4/2018 | Rubinchik et al. |
| 9,962,220 B2 | 5/2018 | Domankevitz |
| 10,069,272 B2 | 9/2018 | Bhawalkar et al. |
| 10,085,814 B2 | 10/2018 | Azoulay |
| 10,149,984 B2 | 12/2018 | Modi et al. |
| 10,305,244 B2 | 5/2019 | Sierra et al. |
| 10,426,564 B2 | 10/2019 | Azoulay |
| 10,434,324 B2 | 10/2019 | Mikrov et al. |
| 10,448,961 B2 | 10/2019 | Preiss et al. |
| 10,478,264 B2 | 11/2019 | Azoulay |
| 10,492,862 B2 | 12/2019 | Domankevitz |
| 10,517,676 B2 | 12/2019 | Schuster |
| 10,561,464 B2 | 2/2020 | Koifman et al. |
| 10,561,570 B2 | 2/2020 | Eckhouse et al. |
| D878,554 S | 3/2020 | Preiss et al. |
| 10,622,780 B2 | 4/2020 | Shang et al. |
| 10,624,699 B2 | 4/2020 | Schomacker et al. |
| 10,729,496 B2 | 8/2020 | Hunziker et al. |
| 10,864,380 B1 | 12/2020 | Karavitis et al. |
| 11,253,720 B2 | 2/2022 | Karavitis et al. |
| 11,738,206 B2 | 8/2023 | Karavitis et al. |
| 2001/0007068 A1 | 7/2001 | Ota et al. |
| 2002/0035360 A1 | 3/2002 | Connors et al. |
| 2002/0091377 A1 | 7/2002 | Anderson et al. |
| 2002/0123745 A1 | 9/2002 | Semmens |
| 2002/0161357 A1 | 10/2002 | Anderson et al. |
| 2002/0173782 A1 | 11/2002 | Cense et al. |
| 2003/0032950 A1 | 2/2003 | Altshuler et al. |
| 2003/0199859 A1 | 10/2003 | Altshuler et al. |
| 2004/0034319 A1 | 2/2004 | Anderson |
| 2004/0034341 A1 | 2/2004 | Altshuler et al. |
| 2004/0073079 A1 | 4/2004 | Altshuler et al. |
| 2004/0093042 A1 | 5/2004 | Altshuler et al. |
| 2004/0167499 A1 | 8/2004 | Grove et al. |
| 2004/0167501 A1 | 8/2004 | Island et al. |
| 2004/0176754 A1 | 9/2004 | Island et al. |
| 2004/0176823 A1 | 9/2004 | Island et al. |
| 2004/0176825 A1 | 9/2004 | Vaynberg et al. |
| 2005/0171581 A1 | 8/2005 | Connors et al. |
| 2005/0215988 A1 | 9/2005 | Altshuler et al. |
| 2005/0251118 A1 | 11/2005 | Anderson et al. |
| 2006/0122668 A1 | 6/2006 | Anderson et al. |
| 2006/0149343 A1 | 7/2006 | Altshuler et al. |
| 2006/0206103 A1 | 9/2006 | Altshuler et al. |
| 2007/0038206 A1 | 2/2007 | Altshuler et al. |
| 2007/0073308 A1 | 3/2007 | Anderson et al. |
| 2007/0159592 A1 | 7/2007 | Rylander et al. |
| 2007/0213695 A1 | 9/2007 | Perl et al. |
| 2008/0004611 A1 | 1/2008 | Houbolt et al. |
| 2008/0009842 A1 | 1/2008 | Manstein et al. |
| 2008/0009923 A1 | 1/2008 | Paithankar et al. |
| 2008/0058783 A1 | 3/2008 | Altshuler et al. |
| 2008/0058784 A1 | 3/2008 | Manstein et al. |
| 2008/0080585 A1 | 4/2008 | Glebov et al. |
| 2008/0119829 A1 | 5/2008 | Okawa |
| 2008/0140164 A1 | 6/2008 | Oberreiter et al. |
| 2008/0188914 A1 | 8/2008 | Gustavsson |
| 2008/0214988 A1 | 8/2008 | Altshuler et al. |
| 2008/0215040 A1 | 9/2008 | Paithankar et al. |
| 2008/0319430 A1 | 12/2008 | Zenzie et al. |
| 2009/0024193 A1 | 1/2009 | Altshuler et al. |
| 2009/0043294 A1 | 2/2009 | Island et al. |
| 2009/0069871 A1 | 3/2009 | Mahadevan-Jansen et al. |
| 2009/0105699 A1 | 4/2009 | Angeley et al. |
| 2009/0112192 A1 | 4/2009 | Barolet et al. |
| 2009/0182397 A1 | 7/2009 | Gustavsson |
| 2010/0049178 A1 | 2/2010 | Deem et al. |
| 2010/0152719 A1 | 6/2010 | Fujikawa |
| 2010/0179521 A1 | 7/2010 | Ghaffari |
| 2010/0249772 A1 | 9/2010 | Mehta et al. |
| 2010/0276609 A1 | 11/2010 | Fertner et al. |
| 2011/0004201 A1 | 1/2011 | Nuijs et al. |
| 2011/0137230 A1 | 6/2011 | Altshuler et al. |
| 2011/0208180 A1 | 8/2011 | Brannan |
| 2012/0022518 A1 | 1/2012 | Levinson |
| 2012/0116271 A1 | 5/2012 | Caruso et al. |
| 2012/0116373 A1 | 5/2012 | Moench et al. |
| 2013/0060309 A1 | 3/2013 | Bradley |
| 2013/0066309 A1 | 3/2013 | Levinson |
| 2013/0066403 A1 | 3/2013 | Giraud et al. |
| 2013/0103017 A1 | 4/2013 | Weckwerth et al. |
| 2013/0079684 A1 | 6/2013 | Rosen et al. |
| 2013/0184693 A1 | 7/2013 | Neev |
| 2013/0261620 A1 | 10/2013 | Brannan et al. |
| 2014/0005760 A1 | 1/2014 | Levinson et al. |
| 2014/0257443 A1 | 9/2014 | Baker et al. |
| 2014/0277219 A1 | 9/2014 | Nanda |
| 2014/0277302 A1 | 9/2014 | Weber et al. |
| 2014/0316393 A1 | 10/2014 | Levinson |
| 2014/0379052 A1 | 12/2014 | Myeong et al. |
| 2015/0202454 A1 | 7/2015 | Burnett |
| 2015/0216816 A1 | 8/2015 | O'Neil et al. |
| 2015/0223975 A1 | 8/2015 | Anderson et al. |
| 2015/0265492 A1 | 9/2015 | Eckhouse et al. |
| 2015/0328077 A1 | 11/2015 | Levinson |
| 2016/0051401 A1 | 2/2016 | Yee et al. |
| 2016/0270848 A1 | 9/2016 | Varghese et al. |
| 2016/0310756 A1 | 10/2016 | Boll et al. |
| 2017/0063468 A1 | 3/2017 | Guo et al. |
| 2017/0304645 A1 | 10/2017 | Schomacker |
| 2018/0036029 A1 | 2/2018 | Anderson et al. |
| 2018/0071024 A1 | 3/2018 | Harris |
| 2018/0140866 A1 | 5/2018 | Daly et al. |
| 2018/0177550 A1 | 6/2018 | Anderson et al. |
| 2019/0000529 A1 | 1/2019 | Kothare et al. |
| 2019/0374791 A1 | 12/2019 | Tagilaferri et al. |
| 2020/0256747 A1 | 8/2020 | Hofvander et al. |
| 2020/0383728 A1 | 12/2020 | Hofvander |
| 2022/0212026 A1 | 7/2022 | Karavitis et al. |
| 2023/0372729 A1 | 11/2023 | Karavitis et al. |

FOREIGN PATENT DOCUMENTS

| | | |
|---|---|---|
| WO | 2008039557 A1 | 4/2008 |
| WO | 2008143678 A1 | 11/2008 |
| WO | 2014149021 A2 | 9/2014 |
| WO | 2014151872 A2 | 9/2014 |

OTHER PUBLICATIONS

Bashkatov, A. N., "Optical Properties of Human Skin, Subcutaneous and Mucous Tissues in the Wavelength Range From 400 to 2000 nm," J. Phys D: Appl. Phys., vol. 38, 2543-2555 (2005), Institute of Physics Publishing, UK.

Dewhirst, M.W. et al., "Basic Principles of Thermal Dosimetry and Thermal Thresholds for Tissue Damage from lyperthermia," Int. J. Hyperthermia, vol. 19 No. 3, May-Jun. 2003, 267-294, T&F Online, UK.

Jacques, Steven L., and Daniel J. McAuliffe, "The Melanosome: Threshold Temperature For Explosive Vaporization and Internal Absorption Coefficient During Pulsed Laser Irradiation," Photochemistry and Photobiology, vol. 53, No. 6, 769-775 (1991), Pergamon Press plc, UK.

Keller, M. D. et al., "In Vitro Testing of Dual-Mode Thulium Microsurgical Laser," Photonic Therapeutics and Diagnostics VIII, ed. N. Kollias et al., Proc. of SPIE, vol. 8207, 820711-1 through 820711-8, 2012.

Li, X. C. et al., "Optical Properties of Edible Oils Within Spectral Range From 300 to 2500 nm Determined by Double Optical Pathlength Transmission Method," Applied Optics, vol. 54, No. 13, May 1, 2015, Optical Society of America, US.

Lloyd, Jenifer R., and Mirko Mirkov, " Selective Photothermolysis of the Sebaceious Glands for Acne Treatment," Lasers in Surgery and Medicine, vol. 31, 115-120 (2002), Wiley-Liss, Inc.

Paithankar, Dilip Y. et al., "Acne Treatment With a 1,450 nm Wavelength Laser and Cryogen Spray Cooling," Lasers in Surgery and Medicine, vol. 31, 106-114 (2002), Wiley-Liss, Inc.

(56) References Cited

OTHER PUBLICATIONS

Paithankar, Dilip Y. et al., "Subsurface Skin Renewal by Treatment With a 1450-nm Laser in Combination With Dynamic Cooling," Journal of Biomedical Optics, vol. 8, No. 3, 545-551, Jul. 2003 Lasers in Surgery and Medicine, vol. 31, 106-114 (Jul. 2003), SPIE.
Pearce, John A., "Relationship Between Arrhenius Models of Thermal Damage and the CEM 43 Thermal Dose," in Energy-Based Treatment of Tissue and Assessment V, ed. Thomas P. Ryan, Proc of SPIE vol. 7181, 718104-1 through 718104-15 (2009), SPIE.
Sakamoto, Fernanda H. et al., "Selective Photothermolysis to Target Sebaceous Glands: Theoretical Estimation of Parameters and Preliminary Results Using a Free Electron Laser," Lasers in Surgery and Medicine, vol. 44, 175-183 (2012), Wiley Periodicals, Inc.
Salomatina, Elena et al., "Optical Properties of Normal and Cancerous Human Skin in the Visible and Near-Infrared Spectral Range," J. Biomed. Optics., 11(6), Nov./Dec. 2006, 064026-1 through 064026-9, SPIE.
Tanghetti, Emil, Oral presentation, "A Histological Evaluation of Sebaceous Gland Damage With a 1726 nm Laser," Abstract Session, Clinical Applications-Cutaneous, Mar. 29, 2019, ASLMS 2019, Americal Society for Laser Medicine & Surgery, Inc.
Tanghetti, Emil, Oral presentation, "Laser Destruction of Sebaceous Glands: Threading the Needle," Special Sessions (CME), Cutting Edge: Laser and Skin, Mar. 30, 2019, ASLMS 2019, Americal Society for Laser Medicine & Surgery, Inc.
Ueno, Koichiro et al., "InSb Mid-Infrared Photon Detector for Room-Temperature Operation," Jpn. J. App. Phys., vol. 52, 092202-1 through 092202-6 (2013), The Japan Society of Applied Physics, Japan.
Vogel, Alfred et al., "Minimization of Thermomechanical Side Effects and Increase of Ablation Efficiency in IR Ablation by Use of Multiply Q-Switched Laser Pulses," Proc. SPIE vol. 4617A, Laser Tissue Interaction XIII,2002.
Wang, Lihong et al., "Monte Carol Modeling of Light Transport in Multi-layered Tissues in Standard C," University of Texas M.D. Anderson Cancer Center, XX-YY (1992), Dept. of the Navy, US.
Nelson, J. Stuart et al., "Dynamic Epidermal Cooling During Pulsed Laser Treatment of Port-Wine Stain," Archives of Dermatology, vol. 131, Jun. 1995, 695-700, Americal Medical Association, US.
Saccomandi, Paola et al., "Techniques for Temperature Monitoring During Laser-Induced Thermotherapy: An Overview," International Journal of Hyperthermia, vol. 29, No. 7, Sep. 13, 2019, 609-619, Informa UK Ltd, UK.
Tekscan, "Best Practices in Mechanical Integration of the FlexiForce Sensor", found at: https://www.tekscan.com/products-solutions/sensors.
Tekscan, "Best Practices in Electrical Integration of the FlexiForce Sensor", found at: https://www.tekscan.com/products-solutions/sensors.
Interlink Electronics, "Fsr 400 Series Data Sheet", found at: https://www.interlinkelectronics.com/.
Interlink Electronics, "Enhancing Medical Devices and Personal Healthcare Products with Force Sensing Technology", Feb. 2014, found at: https://www.interlinkelectronics.com/.
Suprapto, S.S. et al., "Low-Cost Pressure Sensor Matrix Using Velostat" 2017 5th ICICI-BME, Bandung, Nov. 6-7, 2017.
Valle-Lopera, Diego Andres et al., "Test and Fabrication of Piezoresistive Sensors for Contact Pressure Measurement" Revista Facultad de Ingenieria, Medellin, Colombia, 82, pp. 47-52, 2017.
Vaissie, Laurent et al., "Bright Laser Diodes Combat Cancer", Bio Optics World, Jul./Aug. 2009.
Thompson, Daniel J., et al., "Narrow Linewidth Tunable External Cavity Diode Laser Using Wide Bandwith Filter", Rev. Sci. Instrum. 83, 023107 (2012).
Ricci, L. et al., "A Compact Grating-Stabilized Diode Laser System for Atomic Physics" Optics Communications, 117 pp. 541-549, 1995.
Wenzel, H. et al., "Design and Realization of High-Power DFB Lasers", Proceedings of SPIE, vol. 5594, Bellingham, WA, pp. 110-123, 2004.
Office Action dated May 15, 2020, U.S. Appl. No. 16/805,761, filed Feb. 29, 2020.
Notice of Allowance dated Aug. 13, 2020, U.S. Appl. No. 16/805,761, filed Feb. 29, 2020.
International Search Report and Written Opinion for Application No. PCT/US2021/020143, dated Jul. 8, 2021, 11 pages.

DERMATOLOGICAL SYSTEMS AND METHODS WITH HANDPIECE FOR COAXIAL PULSE DELIVERY AND TEMPERATURE SENSING

CROSS-REFERENCE TO RELATED APPLICATIONS

This application is a continuation of U.S. patent application Ser. No. 17/120,237, filed Dec. 13, 2020, now U.S. Pat. No. 11,253,720, entitled "Dermatological Systems and Methods with Handpiece for Coaxial Pulse Delivery and Temperature Sensing," which is a continuation-in-part of U.S. patent application Ser. No. 16/805,761, filed Feb. 29, 2020, now U.S. Pat. No. 10,864,380, entitled "Systems and Methods for Controlling Therapeutic Laser Pulse Duration. The present application claims the benefit of priority to both '237 application and the '380 application, which are both incorporated by reference herein in their entirety. The present application is related to U.S. patent application Ser. No. 17/120,159, filed Dec. 12, 2020 and entitled "Systems and Methods for Controlling Therapeutic Laser Pulse Duration".

BACKGROUND OF THE INVENTION

This invention relates generally to laser-based medical treatment systems, and more specifically to handpieces for controlling the temperature of a target skin area in the treatment of dermatological conditions.

A variety of dermatological conditions are treatable using electromagnetic radiation (EMR). Lasers are frequently used as an EMR source to treat a range of conditions including acne vulgaris, abnormal pigmentation, vascular skin conditions (e.g., spider veins), wrinkles and fine lines, dyschromia, and many others. Both pulsed and continuous-wave (CW) laser systems have been used.

Many dermatological EMR systems use a laser to photothermally damage a target tissue while preserving surrounding or adjacent non-targeted tissues or structures. The principle of selective photothermolysis, which involves thermally damaging a target tissue to promote a healing response, has led to the development of a variety of laser applications as standard of care in many medical fields including dermatology.

Damage to a target tissue during photothermolysis involves raising the temperature of the target tissue to a damage threshold temperature for a specified time period. For a desired level of thermal damage, there is a tradeoff between the temperature the target tissue must reach and the time that the temperature must be maintained. The same thermal damage may be achieved using a lower temperature if the time of heating is increased; if a higher temperature is used, a shorter heating time can achieve an equivalent thermal damage. To avoid thermal damage to non-targeted tissue, it is desirable to limit the heating time to the thermal relaxation time (TRT) of the target tissue, which is the time required for the target to dissipate about 63% of the thermal energy received from the laser pulse. TRT is related to the size of the target chromophore, and may range from a few nanoseconds for small chromophores such as tattoo ink particles, to hundreds of milliseconds for large chromophores such as leg venules. The TRT for a target tissue may be used for a particular laser system to select appropriate damage threshold temperatures for a desired level of thermal damage. For example, depending upon factors such as the laser power, fluence, spot size, etc. used in a given system, a damage threshold temperature to achieve a desired level of photothermolysis at time periods approximately equal to (e.g., slightly longer or shorter than) the TRT may be selected, minimizing damage to non-target tissues.

Photothermolysis can be achieved when three conditions are met: 1) the wavelength of the laser is chosen to have a preferential absorption in the target tissue over non-target tissue; 2) the laser pulse duration should be equal to or less than (=<) the TRT of the target tissue; and 3) the laser fluence (i.e., energy per unit area) must be sufficient to exceed the thermal damage threshold of the target tissue. Together, these principles permit laser systems to be developed that deliver energy at specific wavelengths, pulse durations, and fluences to provide controlled energy to damage target tissue while leaving non-targeted surrounding tissues and structures substantially unaffected.

Selectivity as well as overall safety would be improved if the temperature of the skin could be dynamically controlled. In particular, most laser-based dermatological treatment systems do not provide reliable control of the temperature of the skin during treatment, since pulse durations and the number of pulses applied to a target treatment area are typically user-selected by a user and maintained for a given treatment session until manually changed by the user (e.g., a laser technician, physician, nurse, etc.). There is a need for laser-based treatment systems providing better control of the skin temperature. Some embodiments of the present invention achieve this by using a handpiece capable of cooling the skin surface and measuring the actual skin temperature to dynamically control the temperature during a treatment.

Ideally, thermal damage is highly localized to only the particular target tissue (e.g., a particular skin layer at a particular location, or particular structures such as chromophores within a skin layer at a particular location), with nearby non-targeted tissues/structures remaining unaffected and available to facilitate the healing response in the targeted tissue. However, the structural complexity of the skin, which includes a variety of layers each having unique structural and functional characteristics, has limited the development of effective EMR-based treatments for many skin conditions.

Effectively reaching and limiting thermal damage to target structures within skin tissue by laser radiation is complicated by a variety of intrinsic and extrinsic factors. Intrinsic factors include, without limitation, the depth of the target structure within tissue and the associated absorption of light by non-targeted structures overlying the target (which may involve a plurality of intervening structures each having different light absorption and thermal characteristics), the scattering of light within the skin above the target, the TRT of the target structure and intervening non-target structures, and the removal (or non-removal) of heat by blood flowing through dermal and subdermal layers. Extrinsic factors include, also without limitation, the wavelength, pulse width, power, fluence, spot size, and other characteristics of the laser used to treat the target tissue or structure.

Acne vulgaris, more commonly referred to simply as acne, is the most common reason for office visits to dermatologists in the United States. Over 60 million Americans suffer from acne. Treatment options include topical applications such as disinfectants (e.g., benzoyl peroxide), retinoids (e.g., Retin-A), and antibiotics (e.g., clindamycin and erythromycin), as well as ingested compounds such as antibiotics (e.g., tetracycline), hormonal treatments (e.g., birth control pills), isotretinoin (Accutane, which has significant side effects), and optical treatments such as lasers. Laser treatments have the benefit of avoiding the side effects and inconvenience of pharmaceuticals and topical treatments but, at present, have limited effectiveness for reasons including the previously noted complexity of skin tissue structures and limitations of existing laser systems. More recently, nanosphere particles have been deposited into skin pores and/or follicles, followed by heating of the nanoparticles with laser light to treat acne. Photodynamic therapies, in which an agent is applied to the skin to increase its sensitivity to light, have also been used in conjunction with laser or other light (e.g., blue light) to treat acne.

There is a need for improved laser systems having greater efficacy for treating acne. The present invention discloses systems and methods using laser handpieces to achieve improved treatments for a variety of medical conditions including, without limitation, acne. In one aspect, the present disclosure provides laser system having handpieces providing improved skin temperature control to avoid damage to non-targeted structures and more precisely control thermal damage to target structures. In one aspect, the disclosure provides systems and methods having a laser source, a handpiece to cool and deliver laser pulses to a target skin area, and a temperature determination unit to monitor the target skin temperature. In one embodiment, the handpiece includes optical elements to direct laser pulses to the target tissue along a first optical path, and a temperature determination unit determine the surface temperature of the target tissue using infrared (IR) energy radiated from the tissue along a second optical path. The surface temperature may be determined before, during, or after the delivery of the laser pulses. In one embodiment, the temperature of a target temperature area is determined a plurality of times before and during the delivery of a laser pulse. In preferred embodiments, the first and second optical paths have a common optical axis for at least a portion of each optical path.

Precise temperature control of the target skin area becomes highly important when the patient's skin varies in thickness or composition, such that target skin areas (e.g., spots to which one or more laser pulses are applied) may reach significantly different temperatures when the same laser pulse is applied to different skin areas. The disparity in skin temperatures for a pre-defined laser pulse for different skin areas is magnified when a target structure (e.g., a sebaceous gland or sebum) is deeper in the skin, because of the greater scattering and absorption of energy by overlying tissue that occurs at greater skin depths.

Heating in tissues depends upon both the absorption of the irradiated tissue structures for the wavelength of laser light used, as well as their thermal relaxation times, which is a measure of how rapidly the affected structure returns to its original temperature. By delivering the laser energy in a pulse with a time duration less than the TRT of the target tissue, highly localized heating (and destruction) of a tissue target structure (e.g., melanin, sebum, sebaceous gland, collagen) can be achieved, minimizing damage to non-target structures (e.g., non-targeted skin layers, blood vessels, etc.). If the laser pulse duration is less than the TRT of the target tissue, no significant heat can escape into non-target structures, and damage to non-target structures is limited.

For deeper target structures such as sebaceous glands, which often range from 0.3-2.0 mm (more commonly 0.5-1.0 mm) below the outer surface of the epidermis, damage to overlying tissue structures is difficult to control or limit, since the laser energy must pass through those tissue structures before reaching the target tissue structures. The overlying tissue structures absorb energy depending upon their respective depths and absorption coefficients, and undesired damage may frequently occur. In some instances, the target structures are either sufficiently shallow, or the treatment temperature to which the target structures are raised is sufficiently low, that the heating of overlying structures may not cause excessive damage. Even where the risk of overheating the overlying structures of a relatively deep target is minimal, however, accurate temperature control of the target structure may be poor, resulting in overheating or underheating or the target structure, discomfort to the patient, or a combination of such undesired effects.

The skin surface may be cooled to limit the temperature increase (and damage) to non-target overlying structures, and to limit patient discomfort or pain. However, existing systems lack precise control of the cooling process. Achieving both a desired level of photothermal damage to deeper target structures and minimizing damage to non-target overlying structures has proven elusive. In many cases, the skin is cooled either too much—in which case the deeper target structure fails to reach a temperature damage threshold—or too little, in which case non-target overlying structures are damaged and the deeper target structure may be excessively damaged. There is a need for laser-based treatment systems having improved temperature control of the cooling process to ensure that target structures reach a desired temperature (e.g., a thermal damage temperature) and that thermal damage to non-target structures is minimized or controlled to an acceptable level. There is a need for dermatological laser systems that are able to efficiently treat a variety of medical conditions to achieve these goals.

SUMMARY

In one embodiment, the invention comprises a system for treating the skin of a patient with one or more therapeutic laser pulses, the system comprising: a) a laser source adapted to generate at least one therapeutic laser pulse for application to a target skin area; b) a handpiece optically coupled to the laser source to receive the at least one therapeutic laser pulse from the laser source and to direct the at least one therapeutic laser pulse to the target skin area along a first optical path, the handpiece comprising: 1) a first optical element comprising a reflective element and having a first open area through which said first optical path passes, wherein the first open area comprises one of an aperture and a slot; 2) at least a second optical element comprising at least one of a refractive element and a reflective element, wherein the first optical path engages the at least a second optical element; 3) a contact cooling unit comprising a cooling window adapted to contact and cool a first skin area of the patient from a first temperature to a second temperature, wherein the cooling window comprises a thermally conductive material that is transmissive to infrared energy and the laser pulses, the first optical path passes through the cooling window, and the target skin area comprises a fraction of the first skin area; and c) a temperature determination unit for determining a surface temperature of the target skin area based on infrared energy radiated from the target skin area through the cooling window along a second optical path sharing a common optical axis with the first optical path for at least a portion of the first and second optical paths, the temperature determination unit comprising: 1) a temperature sensing element for sensing infrared energy radiated through the cooling window along the second optical path, the temperature sensing element generating a first signal indicative of the infrared energy radiating along the second optical path, wherein the infrared energy radiating along the second optical path engages the at least a second optical element and is reflected by the first optical element to be detected by the temperature sensing element; and 2) a processor adapted to determine the surface temperature of the target skin area at one or more timepoints before, during, or after the application of one or more therapeutic laser pulses based on the infrared energy detected by the temperature sensing element.

In one embodiment, the invention comprises a method for treating the skin of a patient with one or more therapeutic laser pulses, the method comprising: a) providing a laser source for generating one or more therapeutic laser pulses as a laser therapy; b) providing a handpiece optically coupled to the laser source to receive at least one therapeutic laser pulse from the laser source and direct the at least one therapeutic laser pulse to a target skin area along a first optical path, the handpiece comprising; 1) a first optical element comprising a reflective element and having a first open area comprising one of an aperture and a slot through which the first optical path passes; 2) at least a second optical element comprising one of a refractive element and a reflective element; and 3) a contact cooling unit comprising a cooling window adapted to contact and cool a first skin area of the patient, wherein the cooling window comprises a thermally conductive material that is transmissive to infrared energy and to laser light at a first wavelength range, and wherein a target skin area to be treated by the at least one therapeutic laser pulse comprises a portion of the first skin area; c) providing a temperature determination unit adapted to determine a surface temperature of the target skin area based on infrared energy radiated from the target skin area through the cooling window along a second optical path sharing a common optical axis with the first optical path for at least a portion of the first and second optical paths, the temperature determination unit comprising 1) a temperature sensing element adapted to detect infrared energy radiated through the cooling window along the second optical path; and 2) a processor adapted to determine the surface temperature of the target skin area based on the infrared energy detected by the temperature sensing element; d) contacting the first skin area with the cooling window; e) cooling the first skin area from a first temperature to a second temperature using the cooling window; f) generating at least one therapeutic laser pulse having a wavelength within the first wavelength range using the laser source; g) receiving the at least one therapeutic laser pulse from the laser source with the handpiece; h) applying the at least one therapeutic laser pulse to the target skin area, the therapeutic laser pulse passing through the first open area, engaging the at least a second optical element, and passing through the cooling window along the first optical path; i) determining the surface temperature of the target skin area one or more times before, during or after the application of the at least one therapeutic laser pulse by 1) receiving infrared energy radiated from the target skin area along the second optical path using the temperature sensing element, the infrared energy engaging the at least a second optical element and being reflected by the first optical element onto the temperature sensing element; and 2) determining the surface temperature of the target skin area with the processor based on the infrared energy received by the temperature sensing element; j) performing at least one responsive action in response to determining the surface temperature of the target skin area, selected from 1) terminating the application of the at least one therapeutic laser pulse to the target skin area based on the determined surface temperature; 2) indicating the instantaneous surface temperature of the target skin area; 3) indicating a maximum surface temperature of the target skin area; 4) changing at least one parameter of the laser therapy; and 5) indicating when the surface temperature of the target skin area returns to a desired temperature following delivery of one or more therapeutic laser pulses to the target skin area.

In one embodiment, the invention comprises a method for treating the skin of a patient with one or more therapeutic laser pulses, the method comprising: a) providing a handpiece comprising; 1) a first end for receiving at least one therapeutic laser pulse from a laser source; 2) a first mirror having an open area comprising one of an aperture and a slot; 3) at least one second optical element; 4) a contact cooling unit at a second end of the handpiece, comprising a cooling window for contacting and cooling a first skin area; and 5) a temperature sensing element adapted to detect infrared energy radiated through the cooling window; b) contacting the first skin area with the cooling window; c) cooling the first skin area from a first temperature to a second temperature using the cooling window; d) receiving at least one therapeutic laser pulse from a laser source at the first end of the handpiece; e) applying the at least one therapeutic laser pulse to a target skin area within the first skin area by directing the laser pulse along a first optical path within the handpiece, the first optical path passing through the open area of the first mirror, engaging the at least one second optical element, and passing through the cooling window to the target skin area; f) sensing infrared energy radiated from the target skin area along a second optical path generally counterdirectional to the first optical path and sharing a common optical axis with the first optical path for at least a portion of the first and second optical paths, the second optical path passing from the target skin area through the cooling window, engaging the at least one second optical element, and being reflected by the first mirror onto the temperature sensing element; and g) determining the surface temperature of the target skin area one or more times before, during or after the application of the at least one therapeutic laser pulse to the target skin area based on the infrared energy sensed by the temperature sensing element.

DESCRIPTION

Figure 1:
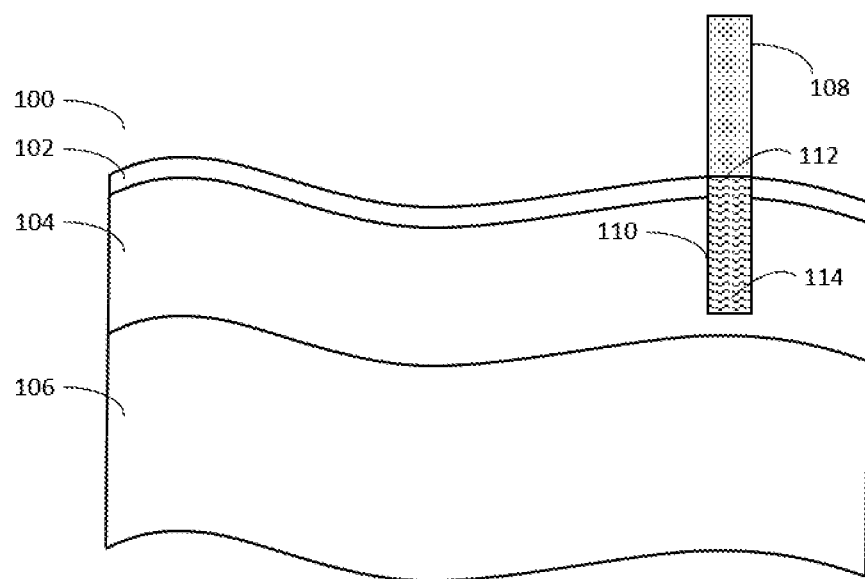
FIG. 1 is a cross-sectional illustration of skin tissue depicting the epidermis, dermis, and hypodermis, with a laser pulse applied to a portion thereof.

Exemplary embodiments of the present disclosure are illustrated in the drawings, which are illustrative rather than restrictive. No limitation on the scope of the technology, or on the claims that follow, is to be implied or inferred from the examples shown in the drawings and discussed herein.

Treatment of many dermatological conditions involve using laser light to heat a target skin area to thermally damage a selected structure within the target skin area and promote a healing response. Consistently accurate delivery of energy to targeted structures to achieve a desired level of damage to the target structure, while minimizing the delivery of energy and corresponding damage to non-targeted structures, has remained an unrealized goal. The present disclosure is directed to providing systems and methods to achieve these objectives.

As used herein "target skin area" refers to the skin receiving the energy of a laser pulse. The target skin area may include the surface skin area illuminated by the laser pulse, as well as deeper structures beneath the surface skin area that receive at least a portion of the energy from the laser pulse. As such, "target skin areas" treated by a laser pulse may refer to a volume of skin as opposed to a true area of an outer surface of the epidermis.

As used herein, "surface temperature" in reference to a target skin area refers to the temperature of the target skin area as determined or measured at or above the surface of the skin. In particular, where infrared (IR) energy radiated from a target skin area is used to measure the temperature of the skin surface, the surface temperature determination includes energy radiated from deeper in the epidermis in addition to the outermost layer of cells. Without being bound by theory, the strong scattering effects of IR wavelengths within the epidermis limit the energy emitted and detected to the upper 100 microns, and primarily the upper portions thereof. Consequently, "determining a surface temperature" based on detection of radiated IR energy refers to the determination of a composite or average temperature of the upper portions (e.g., tens of microns in depth) of the epidermis, and not merely the outermost layer of skin cells. In embodiments of the present invention, IR-based temperature measurements or determinations provides a reliable and precise determination of the temperature of the uppermost portion of the epidermis.

As used herein in connection with optical elements and optical energy, "engages" refers to optical contact between optical energy (e.g., a laser pulse or IR energy) and an optical element such as a lens or a mirror. A laser pulse or IR energy may engage a lens by passing through it, and engages a reflective element by being reflected of its surface.

In one aspect, the present invention comprises systems and methods having a handpiece for improved temperature control of a target skin area during the delivery of one or more therapeutic laser pulses in the treatment of a medical condition. The handpiece is configured to facilitate the delivery of laser pulses traveling in a first direction to a target skin area, and to allow IR energy radiated from the target skin area to travel in a second direction generally opposite ("counterdirectional") to the first direction to detect skin temperature. The handpiece is optically coupled to a laser source adapted to generate at least one, and preferably a plurality, of therapeutic laser pulses for application to the target skin area. The handpiece receives therapeutic laser pulses from the laser source, and includes a cooling window for contacting and cooling a first skin area that includes the target skin area. The cooling window is transmissive to the laser pulses and to IR energy radiated from the target skin area. The laser pulses travel through the handpiece along a first optical path in the first direction, and pass through the cooling window to a target skin area within the first skin area. The system further includes a temperature determination unit that includes a temperature sensing element and a processor for determining a surface temperature of the target skin area based on IR energy radiated from the target skin area through the cooling window along a second optical path travelling along a second optical path generally opposite or counterdirectional to the first optical path. In a preferred embodiment, the first optical path and the second optical path share a common optical axis for at least a portion of their length. The handpiece includes a reflective optical element located in the first optical path and having one of a slot and an aperture through which the laser pulses pass while traveling along the first optical path. The reflective optical element is oriented to receive the IR energy radiated from the target skin area along the second optical path, and to reflect it onto the temperature sensing element. The temperature sensing element generates a signal that is processed by the processor to determine the surface temperature of the target skin area. In a preferred embodiment, the reflective optical element is precisely oriented to receive IR energy from substantially only the target skin area, and not other adjacent tissue within the larger skin area cooled by the cooling window. The handpiece further comprises at least one second optical element within the first optical path, and the laser pulses engage the at least one second optical element. In a preferred embodiment, the at least one second optical element comprises a plurality of optical elements, including at least one lens and at least one reflective element (e.g., a mirror). In a still more preferred embodiment, the IR energy radiated from the target skin area along the second optical path also engages the plurality of optical elements. In various embodiments, the at least one second optical element may comprise elements for focusing, splitting, redirecting, collimating, or performing other operations on the laser pulses and/or IR energy.

In some embodiments, the present invention comprises systems and methods for determining or measuring a surface temperature of a target skin area of a patient during a laser treatment using a handpiece that provides contact cooling of the skin and surface temperature sensing of substantially only a target skin area receiving laser energy. In some embodiments, the present invention provides improved temperature control of a target non-surface (i.e., deeper) structure in the target skin area of a patient during the laser treatment. By providing accurate temperature control of a target skin area during the delivery of laser pulses, the invention provides systems and methods with improved efficacy, safety and/or comfort to patients being treated for a range of dermatological conditions.

In one aspect, the invention provides systems and methods of controlling a temperature of a target skin area during a laser treatment to avoid one or more of overheating or excessively damaging the target area, underheating the target structure, or causing undesired damage to overlying non-targeted structures.

In one aspect, the present invention discloses systems and methods for minimizing the temperature increase of non-target structures overlying a target structure within a target skin area during the delivery of a laser one or a plurality of laser treatment pulses to raise the target structure from a first temperature to a second temperature (e.g., a damage threshold temperature).

In various embodiments, systems of the present invention may determine the temperature of a target skin area one or a plurality of times before, during, or after treatment of the target skin area using IR energy radiated from the skin. The laser treatment may comprise comprises one pulse, or a plurality of pulses comprising a single heating episode of the target skin area. As used herein, a "single heating episode" involves a plurality of pulses where the first pulse raises the temperature of the target skin area from a first or baseline temperature immediately prior to the first pulse, and each successive pulse in the heating episode is applied before the target skin area returns to the first or baseline temperature. Where a plurality of pulses is used to heat the target skin area in a single heating episode, the temperature of the target skin area may be determined during a pulse, between pulses, or a combination of during and between pulses of the single heating episode.

As used in connection with temperature determinations, "real-time" refers to temperature determinations (e.g., temperature measurements or calculations based on data from an IR temperature sensor) performed with little time delay (e.g., less than 100 msec, more preferably less than 5 msec, most preferably 1 msec or less) between the initiation and conclusion of temperature determination. Stated differently, real-time temperature determinations are those made very rapidly and capable of use by the system to perform one or more tasks, such as terminating a treatment of a target skin area, logging the skin temperature profile vs time to a memory, or providing a warning indication to a user.

In one aspect, the invention also comprises contact cooling applied to an external surface of a first skin area to enable heating of deeper structures (e.g., a sebaceous gland) to a damage threshold temperature, while minimizing the heating of overlying non-targeted tissue structures. Real-time temperature determinations may occur during before, during, or after the cooling of a first skin area, and may be used (e.g., by a processor executing a treatment algorithm) to perform a responsive action such as initiating, terminating or adjusting the cooling process, initiating or terminating the delivery of one or more laser pulses to a target skin area within the skin area being cooled, or adjusting a parameter of the laser therapy.

In one aspect, the invention comprises a method of treating a patient having one of more dermatological conditions including, without limitation, abnormal pigmentation conditions, acne vulgaris, dyschromia, hyperhidrosis i.e., excessive sweating), pigmented lesions, vascular lesions, and wrinkles and fine lines by controlled heating of a target skin area from a first surface temperature to a second surface temperature sufficient to cause thermal damage to one or more structures in the target skin area. In one embodiment, the duration of a laser treatment pulse is based on determining the surface temperature of the target skin area one or more times before, during, or after the delivery of laser treatment pulses. In one embodiment, a laser treatment pulse is terminated when the second surface temperature reaches a value indicative of a deeper target structure (e.g., a sweat gland) reaching a desired treatment temperature. The second surface temperature corresponding to the target structure reaching its treatment temperature may be determined prior to treatment, e.g., by thermal (mathematical) modeling of the heating of the target skin area as a function of skin depth based on the parameters of the treatment laser such as wavelength, energy flux, and thermal characteristics of the target skin area such as thermal conductivity, the absorption coefficients of various tissue structures and/or chromophores, etc.

In one aspect, the invention comprises a method of treating a patient having acne vulgaris by controlled heating of a target skin area from a first surface temperature to a second surface temperature, where the second surface temperature corresponds to a temperature resulting in thermal damage to one of sebum or a sebaceous gland within the target skin area. In one embodiment, the duration of the laser treatment pulse is based on determining the surface temperature of the target skin area a plurality of times during the delivery of one or more laser treatment pulses. In one embodiment, the laser treatment pulse is terminated when the second surface temperature reaches a value indicative of the deeper sebaceous gland reaching a sebaceous gland treatment temperature. The second surface temperature corresponding to the sebaceous gland reaching the sebaceous gland treatment temperature may be identified by thermal modeling as previously discussed.

FIG. 1 is a side view illustrating a cross-sectional view of a portion 100 of the skin of a patient, including the outermost epidermis 102, the middle layer or dermis 104, and the bottom layer or hypodermis 106. The epidermis 102 has a thickness of about 80-100 μm, which may vary from patient to patient, and even for a single patient depending upon age, health status, and other factors. It includes up to five sub-layers (not shown) and acts as an outer barrier.

The dermis 104 has a thickness of about 1-5 mm (1000-5000 μm). It contains the blood vessels, nerves, hair follicles, collagen and sweat glands within the skin. Because skin conditions frequently involve structures in the dermis, many laser systems must include sufficient energy to penetrate into the dermis to reach those structures. Careful selection of a number of parameters must be made in the design and construction of laser systems to achieve a desired level of damage to a target structure while minimizing or avoiding damage to non-targeted (e.g., overlying) structures. For example, incorrect selection of the laser wavelength, pulse width, energy per pulse, the use (or nonuse) of a seed laser, or the pump energy of the laser source or amplifier may result in undesired damage and poor performance in treating a dermal structure. Numerous other system choices, such as the use or non-use of an articulating arm for delivery of the laser light to a handpiece for application to the skin, may also affect overall system performance.

The lowest layer of the skin is the hypodermis 106, which includes adipose tissue and collagen. The hypodermis 106 helps control body temperature by insulating the structures of the body below the skin. In addition, the hypodermis protects the inner body tissues from damage by absorbing shock and impacts from outside the body. Because the hypodermis contains fat, its thickness varies widely from person to person based on diet, genetic makeup, and other factors.

FIG. 1 depicts a laser beam 108 applied to a target skin area 110 of the skin 100. The target skin area 110 comprises a surface skin area 112, as well as underlying skin tissue 114 that absorbs at least a portion of the energy of the laser beam 108.

Figure 2:
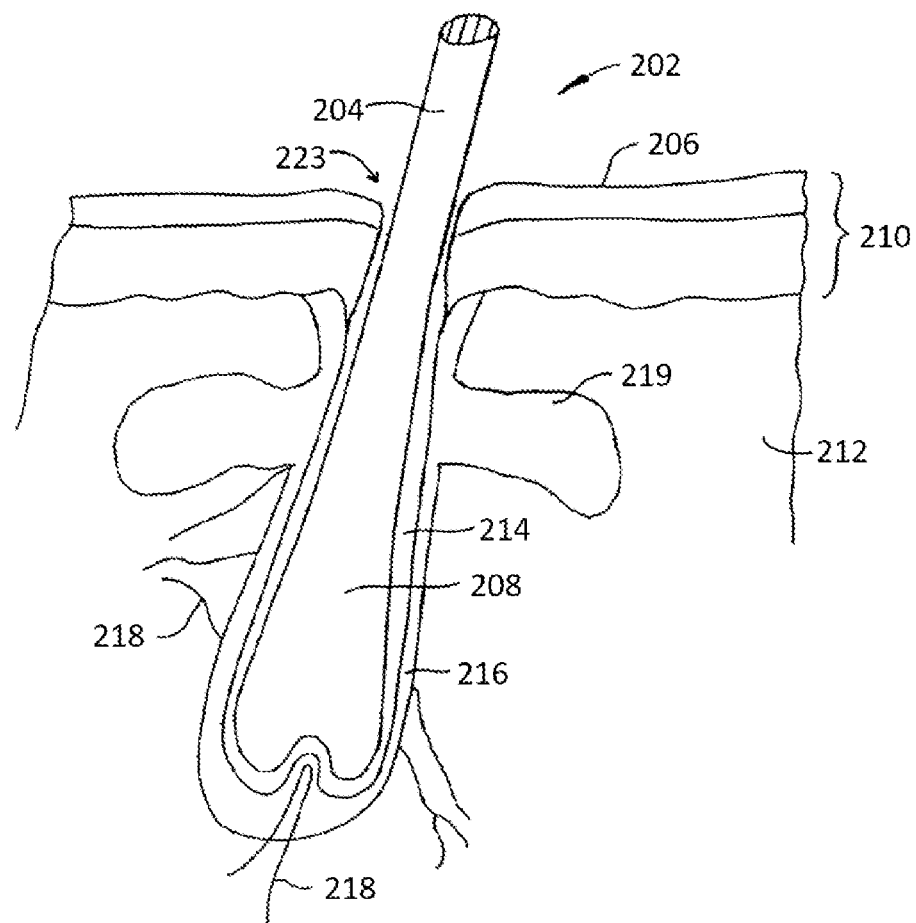
FIG. 2 is a cross-sectional illustration of skin tissue depicting a hair follicle and a sebaceous gland.

FIG. 2 is a side view of the skin of a patient illustrating in simplified form, a hair 202 including a hair shaft 204 extending beyond the exterior skin surface 206. Hair shaft 204 includes a root 208 located below epidermis 210 in the dermis 212. The base, or papilla, of root 208 is located about 4 mm below exterior skin surface 206. Root 208 is housed within hair follicle 214 and is surrounded by tissues including connective tissue sheath 216 and blood vessels 218. Follicle 214 includes a sebaceous gland 219 below an opening 223. Sebaceous glands such as gland 219 are typically located at depths ranging from about 0.3 mm (300 µm) to about 2.0 mm (2000 µm) below exterior skin surface 206, but their depth varies depending upon body location.

Epidermis 210 includes melanin (not shown), a dark pigment found in tissues of the hair, skin and eyes. Melanin, the primary determinant of skin color, is located within globular structures known as melanosomes, which are produced by skin cells called melanocytes. Darker skin has more melanosomes (and thus more melanin) per unit skin area compared to lighter skin. Laser systems targeting deeper structures such as sebaceous gland 219 in the dermis may present a higher risk of patient discomfort where wavelengths having a relatively high absorption coefficient in melanin are used. Without being bound by theory, when laser light at wavelengths readily absorbed by melanin is applied to darker skin (or dark tattoos having ink particles that absorb laser light at similar wavelengths to melanin), the energy absorbed by the melanin (or tattoo ink particles) attenuates part of the laser energy that otherwise would reach deeper structures, heating the skin of the epidermis and/or upper dermis to a greater degree than lighter/untattooed skin. Additional energy—e.g., using higher fluences, higher energy per pulse, or longer treatment times—must be applied to reach and heat deeper structures to a target treatment temperature. However, higher pulse fluences and pulse energy may compound the problem, since the additional energy delivered in a shorter time period will cause the overlying skin temperature to rise even faster than using lower fluences or energies. In addition, longer treatment times can only deliver more energy to the target if the energy is delivered within the TRT of the target tissue—otherwise, the additional energy largely leaks from the target tissue into adjacent non-target tissue.

Accordingly, in one aspect, the present invention provides laser treatment systems to minimize discomfort by adjusting one or more treatment parameters based on the patient's skin type. In one embodiment, the invention provides systems and methods comprising a handpiece for determining a skin type of a patient and automatically adjusting one or more treatment parameters based on the skin type of the patient. This may involve, for patients having darker skin types, one or more of: providing additional cooling of the patient's skin prior to applying a laser therapy to the patient's skin; lowering a first skin temperature at which a therapy pulse is initiated and applied to the patient's skin; lowering a fluence of a laser therapy; lowering a peak power of the laser pulses of a laser therapy; providing a longer pulse width of a pulsed laser therapy; and providing a larger beam diameter for a pulsed laser therapy.

Successful treatment of acne involves damaging sebocytes, sebum and/or sebaceous glands. This involves heating these structures to damage the gland and/or kill bacteria resident therein. Accordingly, in one embodiment the invention provides laser light at a wavelength that is highly absorbed by sebum, compared to competing skin chromophores (e.g., water), to limit the damage to non-targeted tissue and concentrate the laser energy delivered into the targeted sebaceous gland. Because sebaceous glands are relatively deep structures located in the dermis at depths of 300-2000 µm (0.3-2.0 mm), it is desirable to select a wavelength of light capable of non-ablative penetration to these depths.

Figure 3A:
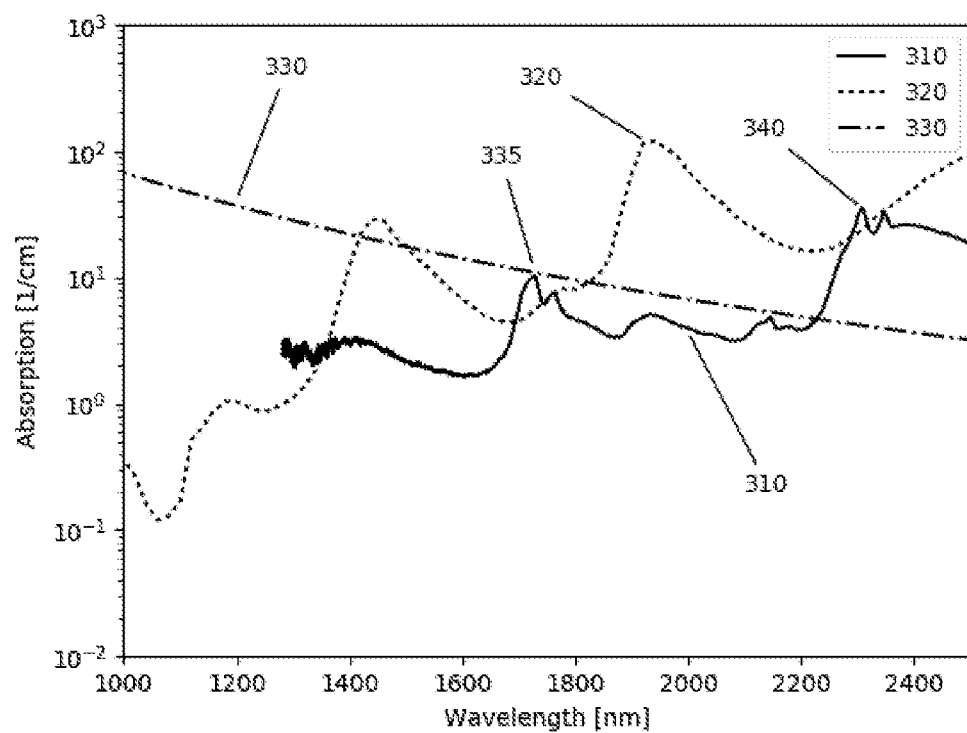
FIGS. 3A and 3B are graphs illustrating the absorption coefficients of human sebum lipid, water, and melanosomes for various wavelengths of light.
Figure 3B:
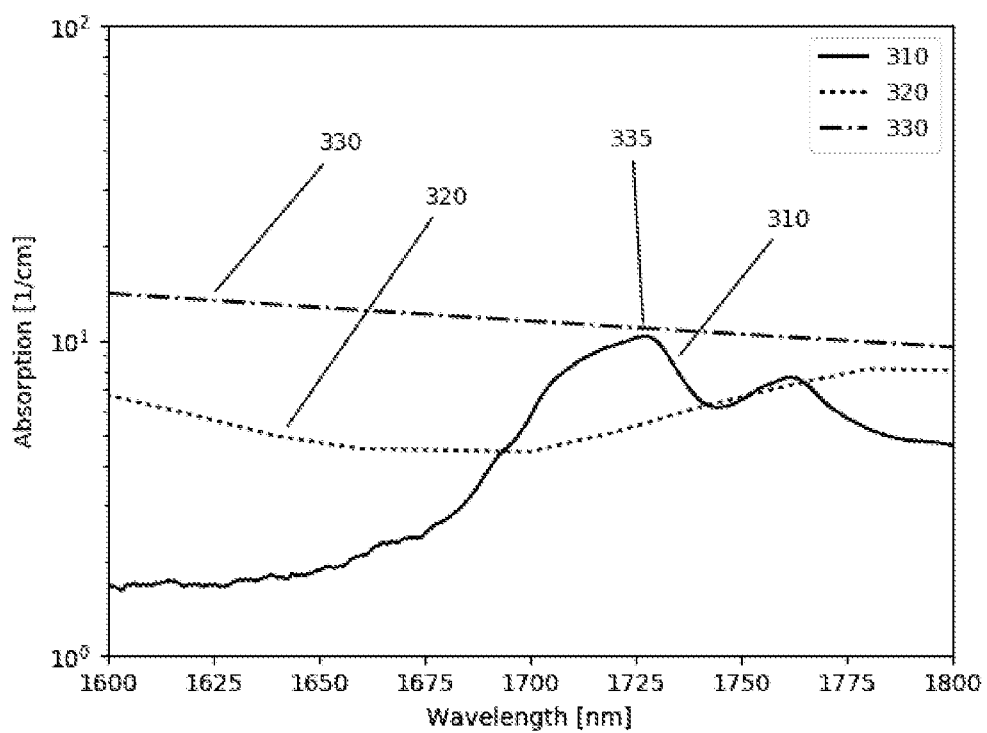

FIGS. 3A and 3B are graphs illustrating the absorption curves for several chromophores of interest (water, sebum, and melanosomes) at wavelengths of light for portions of the near-infrared spectrum (about 750 nm-1400 nm) and the short-wavelength IR spectrum (about 1400-3000 nm). FIG. 3A illustrates the absorption curve 310 for sebum, the water absorption curve 320, and the absorption curve 330 for melanosomes. It will be appreciated that in laser treatment systems directed toward conditions other than acne, e.g., tattoo removal or pigmented lesions, the absorption of other chromophores (e.g., inks of various colors, hemoglobin, etc.) will be important considerations in selecting laser treatment system parameters such as wavelength, fluence, peak power, etc.

FIG. 3A demonstrates that the sebum absorption curve 310 has a peak at about 1727.5 nm, meaning that sebum absorbs laser light at this wavelength more strongly than light at other nearby wavelengths, e.g., 1650 nm or 1800 nm. The absorption coefficient of water is less than that of sebum in a range of from about 1693 nm to about 1742 nm, and within a range of from about 2280-2360 nm. The absorption coefficient of melanosomes exceeds that of sebum at all wavelengths less than about 2225 nm, although only by a small amount at the 1727.5 nm peak for sebum, as demonstrated at point 335 of FIG. 3A, where the two absorptions curves approach one another. It will be appreciated by persons of skill in the art that the concentration of sebum, water, and melanin may vary from patient to patient for a given area, and even within a particular patient depending upon the target tissue structure(s), the hydration status of the patient, and the skin type or area of the patient.

As shown more clearly in FIG. 3B, which is a more detailed illustration of the absorption curves of FIG. 3A for the 1600-1800 nm wavelength region using like numbers for like absorption curves and peaks, the absorption coefficient for sebum (curve 310) at a peak of about 1727.5 nm (point 335) is approximately twice that of water (curve 320), and is only slightly less than that of melanosomes (curve 330). Specifically, the absorption coefficient for melanosomes at 1727.5 is about 11.0 $cm^{-1}$, and that of sebum is about 10.3 $cm^{-1}$. Accordingly, in one embodiment, the invention comprises a laser providing pulsed laser light at a wavelength of between 1693-1742 nm, more preferably at about 1720-1730 nm, and more preferably still at about 1727.5 nm.

Referring again to FIG. 3A, the sebum absorption curve 310 has a further absorption peak (340) of about 2305 nm, exceeding that of both water and melanosomes at the same wavelength. In one embodiment, the invention comprises a laser providing pulsed laser light at a wavelength of between about 2287-2318 nm. Although sebum strongly absorbs light at 2305 nm, light at this wavelength is less suitable because its penetration depth into skin is much less than that of light at 1727.5 nm. In general, at wavelengths shown in FIGS. 3A and 3B, the penetration of light decreases with increasing wavelength. Treatment of acne and other conditions with laser light involves multiple tradeoffs, including the relative absorption coefficients of target and non-target tissues/structures, penetration depth of the wavelength of interest into skin, laser power, laser pulse fluence, pulse duration, pulse frequency, etc.

Figure 4A:
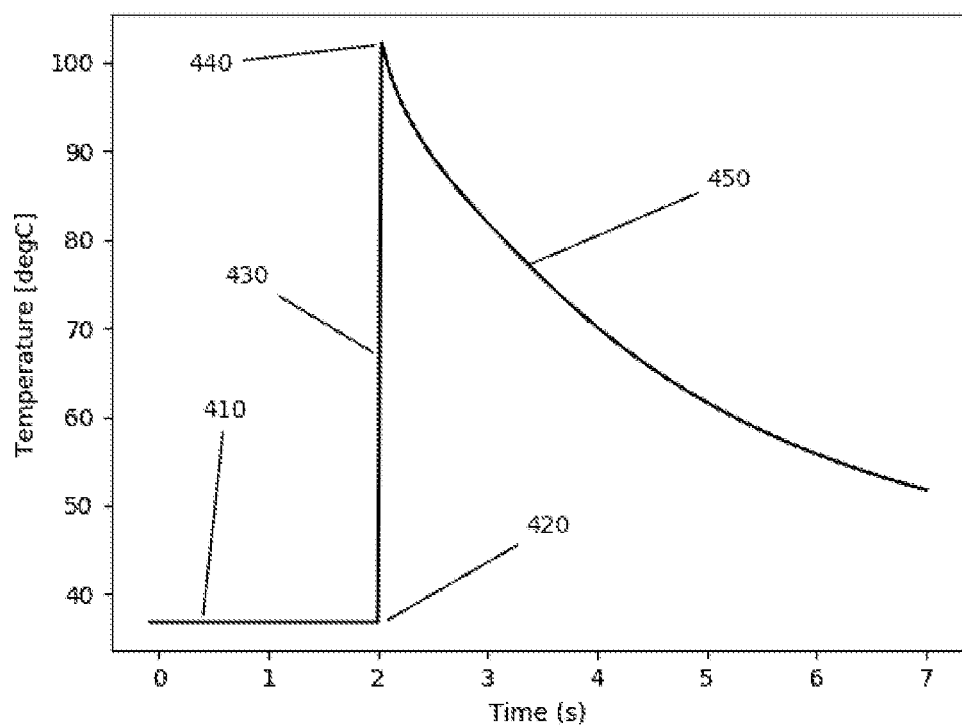
FIG. 4A is a graph illustrating a surface temperature profile of a target skin area according to a mathematical model of a treatment with a laser pulse.
Figure 4B:
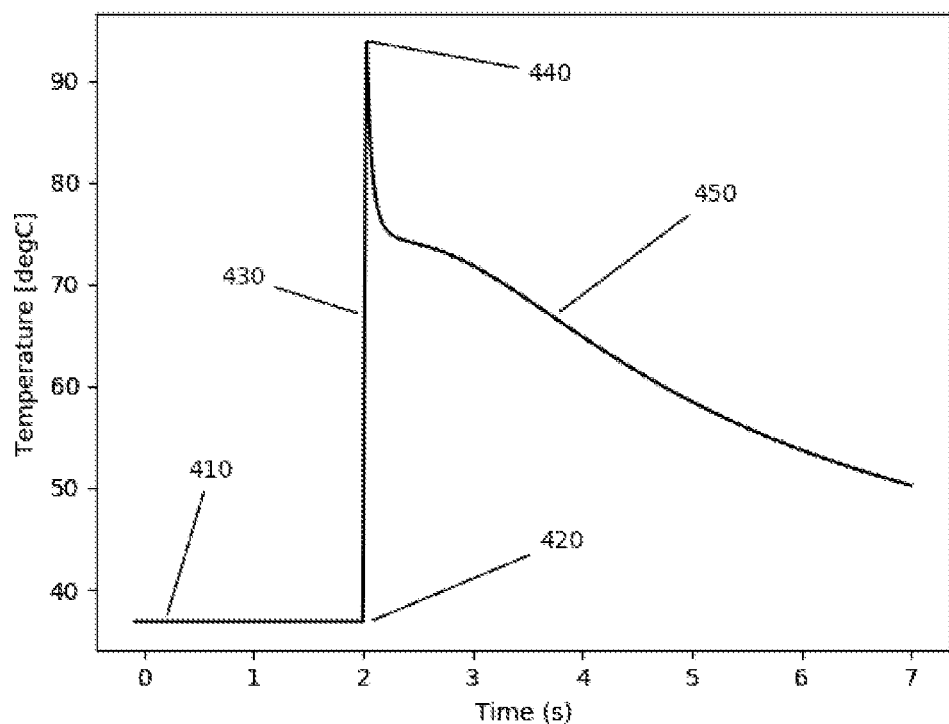
FIG. 4B is a graph illustrating a sebaceous gland temperature profile within a target skin area according to the mathematical model of the laser pulse of FIG. 4A.

FIGS. 4A and 4B illustrate exemplary temperature profiles of the surface of a target skin area (FIG. 4A) and a sebaceous gland (FIG. 4B) located below the surface of the target skin area during a laser pulse according to a mathematical model. The laser pulse is intended to raise the temperature of the sebaceous gland to a temperature to achieve a desired cell population death for sebocytes. In this embodiment, the laser pulse is a tophat pulse (i.e., having a uniform intensity profile over the covered area) with a wavelength of 1727.5 nm, a pulse duration of 30 msec, a beam diameter of 2.8 mm, a power of 75 W, a pulse energy of 2.25 J, and a fluence of 37 J/cm². For purposes of illustration, the skin is depicted as remaining at body temperature for 2 seconds prior to the application of the pulse, although it will be appreciated that any arbitrary time period could be shown.

Referring to FIG. 4A, at time t=2 seconds, a single pulse of laser light having the parameters noted above is initiated and applied to a target skin area, depicted at point 420. The surface temperature of the skin rises during the pulse, as shown by line 430, to slightly above 100° C. as shown by peak 440. After the pulse is terminated, the skin surface temperature of the target area cools rapidly over the next several seconds, as indicated by curve 450, falling to below 60° C. within 4 seconds (t=6 seconds) after the termination of the pulse.

FIG. 4B illustrates the temperature profile of a sebaceous gland located at a depth of 650 µm below the skin surface in the laser pulse model of FIG. 4A. As in FIG. 4A, the skin remains at body temperature for 2 seconds (410) prior to the initiation of a single pulse (421) applied to the target skin area. The temperature of the gland rises during the pulse (430) to a maximum temperature 440 of about 92° C.—less than the surface skin temperature illustrated in FIG. 4A due to scattering and the energy absorbed by the overlying tissue. Because the pulse energy at 1727.5 nm is preferentially absorbed by the sebaceous gland (as discussed in connection with FIGS. 3A and 3B), comparatively more energy from the laser pulse that reaches the gland is absorbed by the oily tissue therein compared to overlying tissue containing a higher water content. Consequently, the temperature profile (450) of the sebaceous gland after termination of the pulse at 440 differs significantly from that of the skin surface temperature depicted in FIG. 4A. Although the temperature initially falls rapidly to about 85° C., the temperature thereafter falls more slowly than the surface temperature shown in FIG. 4A.

The pulse modeled in FIGS. 4A and 4B has energy levels below those necessary to ablate skin tissue. Although the pulse will result in thermal damage to the sebaceous gland and could be used to treat acne, temperatures above 45-50° C. are likely to result in significant discomfort when they persist, as illustrated in FIG. 4A, for 4 seconds or longer. Accordingly, the pulse depicted in FIG. 4A would have limited application as a viable treatment to most patients. In one embodiment, the laser pulses described in connection with FIGS. 4A and 4B result in temperatures too high to be used for treatment, although they could be modified (e.g., by lowering pulse fluences, shortening pulse treatment times, etc.) to result in skin temperatures more suitable for treatment. In one embodiment, temperatures may be lowered by skin cooling, as described in connection with FIGS. 5A and 5B.

Figure 5A:
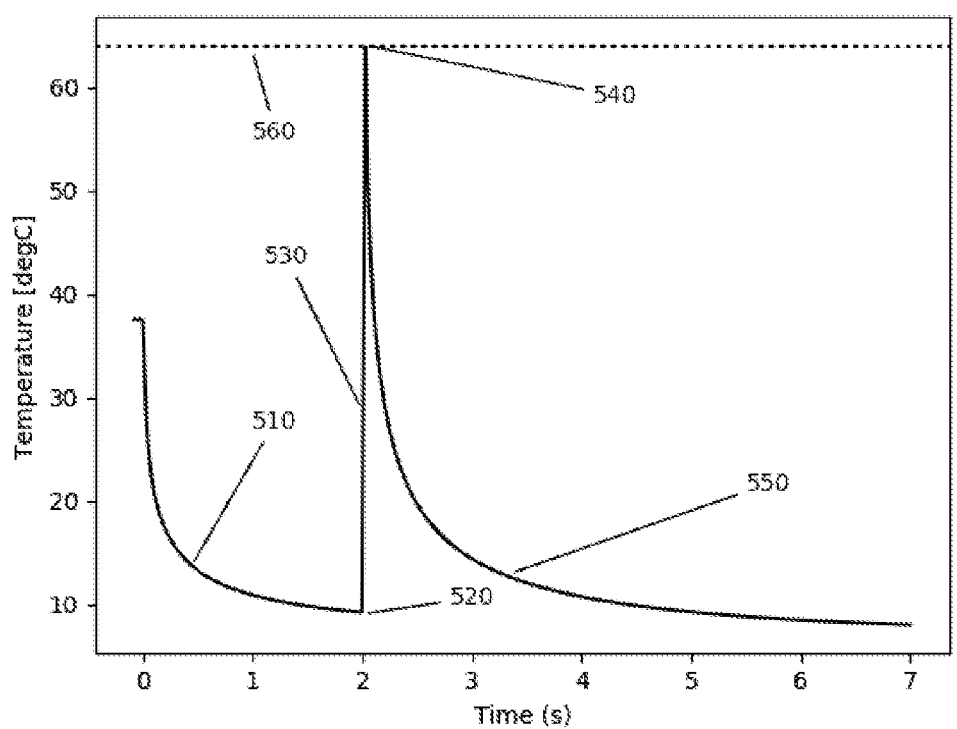
FIG. 5A is a graph illustrating a surface temperature profile of a target skin area before, during, and after a laser pulse treatment with skin cooling, according to a mathematical model.
Figure 5B:
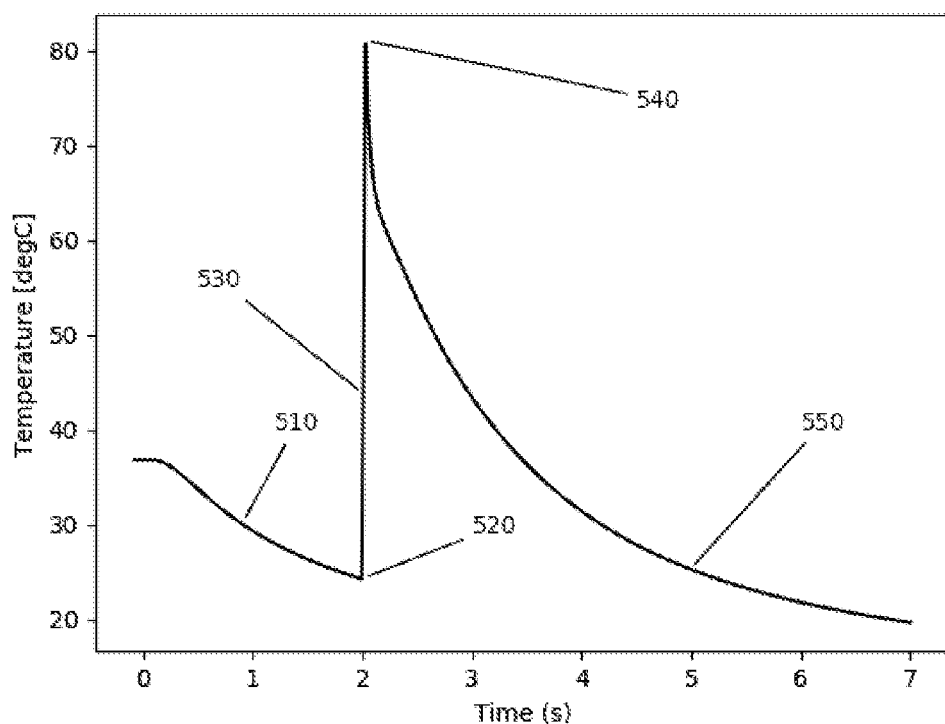
FIG. 5B is a graph illustrating a sebaceous gland temperature profile within a target skin area before, during, and after a laser pulse treatment with skin cooling, according to the mathematical model of FIG. 5A.

FIGS. 5A and 5B illustrate exemplary temperature profiles of a target skin area during a laser pulse according to a different mathematical model than those of FIGS. 4A-B. In the embodiment of FIGS. 5A and 5B, the laser pulse has the same parameters as those of FIGS. 4A-B (wavelength λ=1727.5 nm; pulse duration=30 msec; beam diameter=2.8 mm, power=75 W; pulse energy=2.25 J; fluence=37 J/cm²). However, in FIGS. 5A and 5B the target skin area is cooled prior to, during, and after the application of the laser pulse.

Although many known methods and modes of precooling the skin may be used, the embodiment of FIGS. 5A and 5B are modeled on a system having a contact cooling element applied to a first skin area that includes a target skin area to be treated by the laser pulse. The contact cooling element includes a cooling window that, in some embodiments, directly contacts the first skin area, and the target skin area actually irradiated by the laser pulse is wholly located within the first skin area. Although a variety of materials may be used as the contact cooling window, in the embodiment of FIGS. 5A and 5B, the cooling system includes a sapphire cooling window cooled by a thermoelectrical cooler (TEC) coupled to the window. The sapphire cooling window has a thickness of 3 mm and a diameter of 1 inch (25.4 mm), although many different sizes, shapes, thicknesses, and materials may be used different embodiments. For example, although the cooling window modeled in the embodiment of FIGS. 5A and 5B was circular, other cooling window shapes such as square, rectangular, or other polygonal or nonpolygonal shapes could be used in different embodiments and for different tissue types. The cooling window was modeled as being cooled to a temperature of 5° C.

In alternative embodiments, non-contact cooling systems (e.g., cold air or other fluid circulated onto or across the surface of a target skin area) may be used to cool the skin. However, it is believed that the thermal resistivity of the skin, and the thermal coupling between the skin and gases such as air, typically preclude non-contact systems from providing adequate cooling capacity during the delivery of laser pulses to both effectively treat deeper target structures and prevent the skin surface from reaching temperatures likely to result in significant discomfort. Accordingly, contact cooling systems are preferred. In other embodiments, evaporative cooling systems (e.g., sprayed coolant evaporating from the skin) may be used.

In FIG. 5A, the contact cooling element at 5° C. is applied to the skin at time t=0, and skin temperature falls rapidly along curve 510 to a target temperature of about 10° C. at time t=2 second, at which point (520) the laser pulse is applied to the skin. Delivery of the laser pulse to the target skin area is continued until a target surface temperature 560 of the target skin area is reached (540), at which point the laser pulse is terminated. Because the contact cooling element continues to cool the skin both during and after the laser pulse, the surface temperature falls rapidly along curve 550 after laser pulse termination.

FIG. 5B illustrates the temperature profile of a sebaceous gland located at a depth of 650 µm below the skin surface in the cooling and laser pulse delivery process of FIG. 5A. When contact cooling is applied to the skin at time t=0, the temperature of the gland declines (curve 510), but much less rapidly than the surface temperature, depicted in FIG. 5A. The laser pulse is initiated at point 520, and the temperature of the gland rises along line 530 until the laser pulse is terminated (540). The gland temperature thereafter falls along line 550, but less rapidly than the surface temperature decline following the pulse termination in FIG. 5A.

Because direct measurement of the gland temperature is difficult or impossible given its depth within the skin, in embodiments of the present invention, surface skin temperature may be monitored as an indirect indication of the gland temperature. Because the goal of the laser treatment is to heat the sebaceous gland to a damage threshold temperature, cooling the gland (as opposed to the skin surface) shown by curve 510 in FIG. 5B is undesired, but is an unavoidable consequence of the protective precooling of the overlying skin tissue. Precooling the overlying skin tissue to a desired surface temperature of about 10° C., as shown in FIG. 5A, generates a downward cooling wave in the target skin area, propagating from the skin surface toward the deeper tissues in the dermis and hypodermis. The precooling process may be controlled such that, for a sebaceous gland in a known depth range, when the laser pulse is delivered to heat the target skin area, the precooled overlying skin remains below a damage threshold temperature while the target sebaceous gland reaches (or exceeds) a damage threshold temperature. This is facilitated by selecting a laser wavelength for which the absorption coefficient of sebum/sebaceous gland tissue exceeds that of water, the primary chromophore of most of the overlying dermal and epidermal tissue.

Comparing FIGS. 5A and 5B, precooling the skin allows the sebaceous gland to reach a temperature of about 78° C. at the termination of the laser pulse—about 13° C. above the surface temperature of target skin area at the surface (about 62° C.). Although the overlying tissue is unavoidably heated during pulse delivery, careful precooling before initiating the laser pulse allows the surface temperature to be precooled to a temperature well below the sebaceous gland at pulse initiation (about 10° C. for the skin surface vs. about 22° C. for the sebaceous gland as shown by FIGS. 5A and 5B at point 520). This temperature difference occurs because the cooling window creates a thermal gradient between the skin surface and deeper structures as heat is removed. In addition, the pulse energy at a wavelength of 1727.5 nm is more highly absorbed by the sebaceous gland than overlying tissue. Because of the selective precooling and differential absorption between the surface and the sebaceous gland, the non-targeted overlying tissue is heated by the laser pulse to a lower temperature (about 63° C., FIG. 5A at point 540) than the targeted sebaceous gland (about 81° C., FIG. 5B at point 540), minimizing damage to the non-targeted tissue and patient discomfort.

Figure 5C:
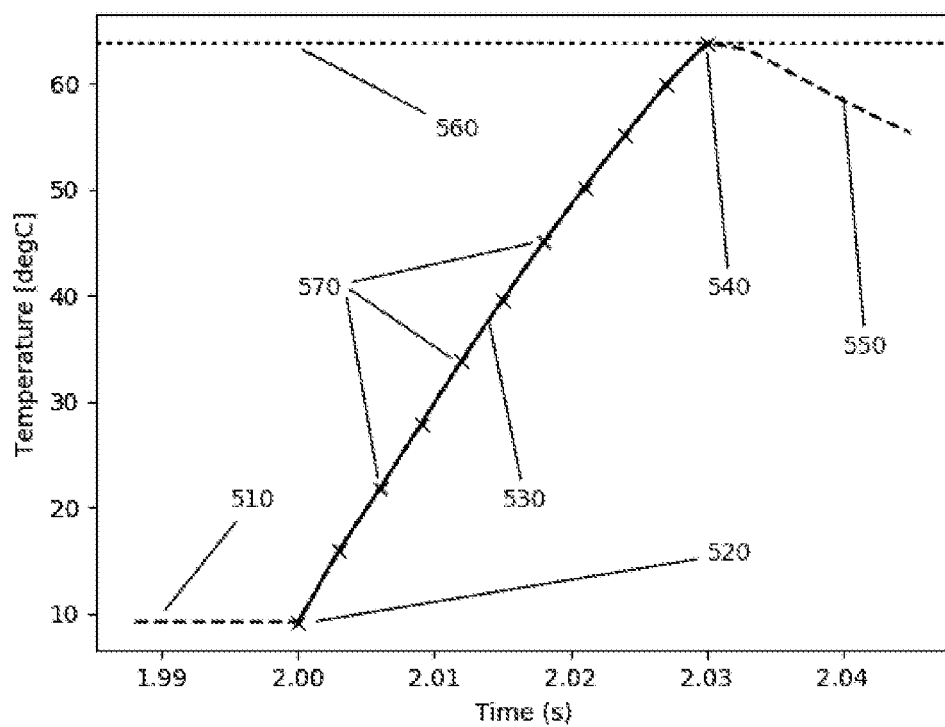
FIG. 5C is more detailed graph illustrating a surface temperature profile for a target skin area during treatment with a laser pulse according to the mathematical model of FIG. 5A.

In some embodiments, the present invention includes a method of controlling the duration of a pulse to limit the surface temperature of a target skin area to a desired or target threshold using a handpiece capable of contact cooling and rapid, real-time temperature measurement of the skin during the delivery of one or more laser pulses. FIG. 5C demonstrates a method of achieving such control by monitoring the temperature of a pulse during the delivery of a single pulse. The surface temperature of the skin may be determined one or more times during pulse delivery, and the pulse may be terminated based on one or more of the skin temperatures. In one embodiment, the skin temperature is periodically determined during the pulse delivery, and the pulse is terminated when the surface skin temperature reaches (or is within a desired interval of) a threshold temperature.

FIG. 5C, illustrates a surface temperature profile during the delivery of the laser pulse of FIG. 5A. From time t=1.99 to t=2.00 seconds, the temperature of the skin near the surface (modeled in FIG. 5C at a depth of 100 μm) is relatively constant at about 10° C. (line 510). At time t=2.00 seconds (520), the pulse is initiated and applied to the skin through the cooling window. Simultaneously, the first of a plurality of surface temperature determinations of the target skin area 570 is made. Pulse delivery continues along line 530, and the surface temperature rises until the pulse is terminated at 540. After pulse termination, the surface temperature falls as indicated by line 550. During pulse delivery, multiple temperature determinations 570 are made at equal intervals, although the frequency of temperature sampling may vary based on a variety of factors such as the time frame desired for heating the tissue, thermal relaxation time of the target structure, pulse fluence, pulse power, pulse wavelength, and exogenous factors such as the target structure damage threshold, and other factors. Temperature determinations may be performed at a desired sampling interval, e.g., 100 msec or less (i.e., 10 or more temperature determinations per second) and may occur at uniform or non-uniform time intervals, e.g., varying based on the difference between a measured temperature and a desired threshold, or on other exogenous factors. In one embodiment, the temperature sampling interval is increased as the surface skin temperature approaches a desired temperature. Depending upon the sensing element and processor used, the surface temperature may be determined at a sampling or time interval of 0.001-100.0 msec (i.e., 1-100,000 μsec, or performing 10 to 1 million temperature determinations per second).

FIGS. 5A and 5B illustrate methods of treating a sebaceous gland according to one embodiment of the present invention. Additional details of treating a sebaceous glans may be found in U.S. Pat. No. 10,864,380, which is incorporated herein by reference. However, embodiments of the present invention may be used to treat other structures in the dermis or hypodermis (e.g., sweat glands, hair follicles, etc.) by facilitating precise control of surface and deeper temperatures within a target skin area.

Figure 6A:
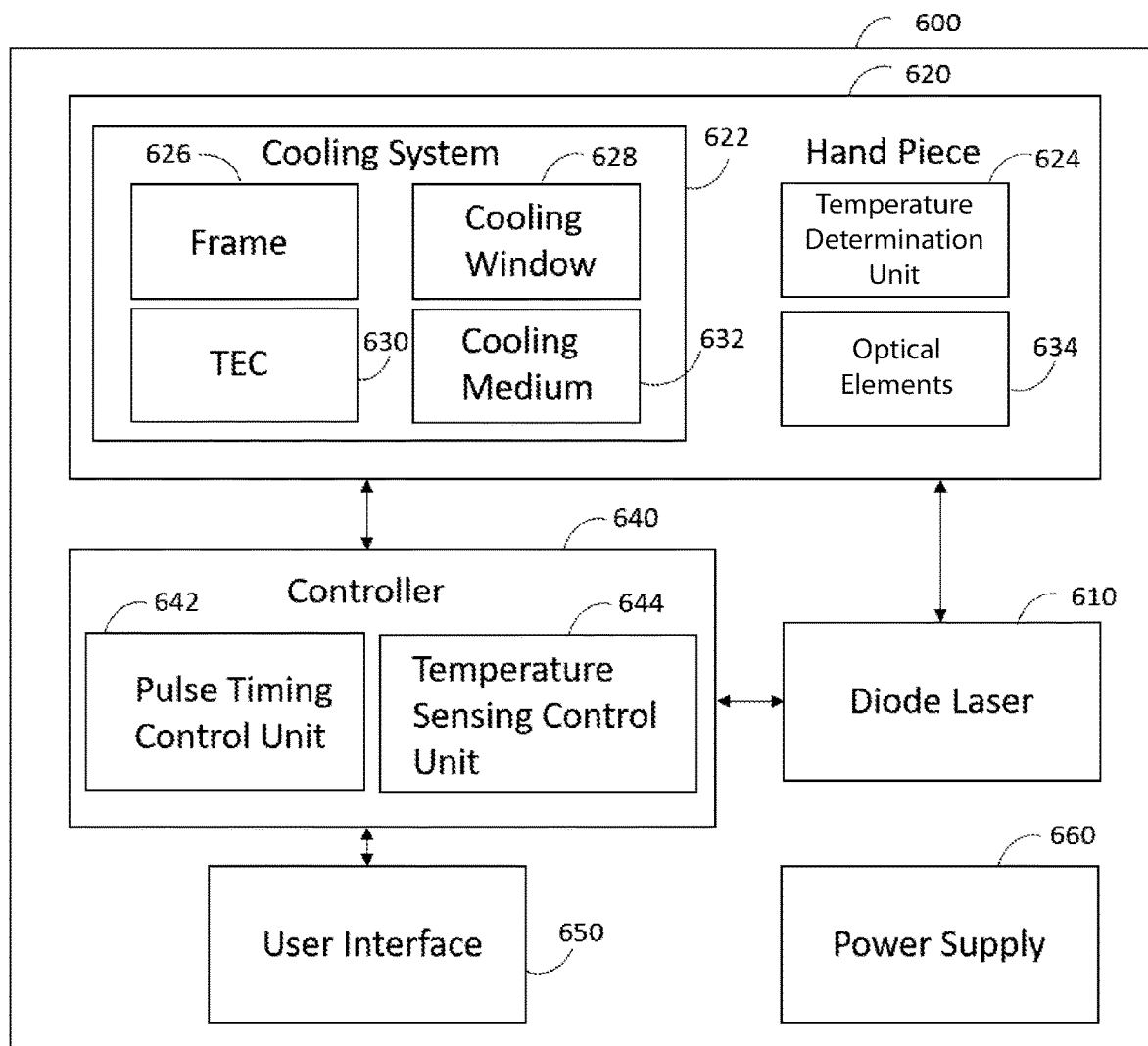
FIGS. 6A and 6B are block diagrams of embodiments of a dermatological treatment system according to the present invention.

FIG. 6A is a schematic illustration, in block diagram form, of an embodiment of a therapeutic laser system 600 having a handpiece with contact cooling and temperature sensing for providing therapeutic laser pulses along a first optical path that is coaxial with a second optical path for sensing skin temperature for at least a portion of the first and second optical paths. A laser 610, which is preferably a semiconductor laser, provides laser pulses having a wavelength with a high absorption coefficient in a target tissue. The target tissue may be sebaceous gland tissue, sweat gland tissue, fat, or other tissue. Laser 610 is optically coupled, e.g., by an optical fiber, articulating arm, or other optical coupling elements known in the art, to a handpiece 620 for delivery of one or more laser pulses to a target skin area. Although semiconductor (e.g., diode) lasers are preferred, it will be appreciated that other laser types (e.g., fiber lasers, dye lasers, etc.) may be used in different embodiments.

Handpiece 620 includes a cooling system 622 for cooling a first skin area that includes a target skin area within the first skin area. Cooling system 622 includes a contact cooling element comprising a cooling window 628 maintained in a fixed position in contact with a heatsink portion of a thermoelectric cooler (TEC) 630 by a window frame 626. Cooling window 628 may comprise any of a variety of IR-transmissive materials, including sapphire, ZnS, diamond, ZnSe, and other thermally conductive material that are transmissive to infrared light. In alternative embodiments (not shown), the contact cooling element may comprise components or structures in addition to cooling window 628, such as a copper (or other material having a high thermal conductivity) cooling element that is not light-transmissive to provide additional cooling capacity.

TEC 630 may be a Peltier-type cooler and has a warm side and a cold side (not shown). The heatsink portion of the TEC 630 is part of the cold side and is used to remove heat from the cooling window 628 to maintain the cooling window at desired temperature as it contacts the first skin area. A cooling medium 632 removes heat from the hot side of the TEC 630 to prevent heat buildup in handpiece 620. In one embodiment, the cooling medium comprises circulating cold water, although other thermally conductive fluids or other materials may be used in different embodiments. In preferred embodiments, the cooling medium is circulated to and from TEC 630 from a reservoir (not shown) that is not part of the handpiece.

To ensure efficient skin cooling, it is necessary to maintain good contact between the skin and the cooling window 628 during treatment. In one embodiment (not shown), the invention comprises one or more contact sensing elements to detect when the cooling window 628 is properly in contact with the first skin area. The contact sensing element(s) may be coupled to, or separate from, cooling window 628 and/or frame 626, and may comprise, e.g., one or more electrical contacts capable of sensing electrical activity, conductivity, or resistance of the skin indicative of adequate skin/cooling window contact. Other contact sensing elements (e.g., ultrasonic sensors) detecting different skin parameters or features associated with proper contact (e.g., force, vibration, pressure, temperature, the presence of sweat or skin oils) may also be used.

One or more skin contact indicators (not shown) may alert a user to the contact status between the skin and cooling window 628. The skin contact indicator may indicate when the contact element(s) are—or are not—in good contact with the first skin area and may prompt the user to manipulate the handpiece to restore good contact when necessary. The skin contact indicator(s) may comprise, e.g., an LED indicator on handpiece 620 that displays a first color when good skin contact exists and a second color when the window 628 is not in proper contact with the skin. Other indicators, such as an audible sound or alarm, may also be provided, and the system may be interlocked such that the system will not apply (or will terminate) a laser pulse if good contact between the cooling window 268 and the skin is absent.

Handpiece 620 further includes a temperature determination unit (TDU) 624 for determining a surface temperature of the target skin area. TDU 624 may, in various embodiments, sense the temperature of the target skin area one or more times before (e.g., during a precooling step), during, or after (e.g., during a postcooling step) laser pulse delivery. During delivery laser pulse(s) to a target skin area, the skin surface temperature may be influenced by two different heating mechanisms, including energy absorbed directly from the laser, and thermal bloom resulting from energy conducted from deeper skin tissue as the thermal energy absorbed by deeper structures relaxes into the environment. Thermal bloom from deeper structures back to the skin surface may be a significant cause of epidermal damage in laser systems targeting relatively deep structures such as sebaceous or sweat glands. Therapeutic laser systems such as system 600 enable improved treatment outcomes by ensuring that the surface temperature of a target skin area remains below a desired surface temperature even while heating deeper structures to higher temperatures, minimizing both skin damage and patient discomfort.

Temperature determination unit (TD) 624 comprises a temperature sensing element for generating a first signal indicative of skin surface temperature, and a processor for processing the first signal to determine the surface temperature. TDU 624 may sense the surface temperature of the target skin area one or more times before, during, or after delivery of laser pulse(s) from laser 610. TDU 624 may be capable of sensing the surface temperature of the target skin area at from 10 to 1 million times per second. In one embodiment, the temperature sensing element of TDU 624 comprises an infrared (IR) radiation detector, shown in FIG. 9A, to detect IR energy radiating from the surface of the target skin area through the cooling window 628, and a processor (e.g., controller 640 as discussed below) to determine the surface temperature of the target skin area based on data received from the temperature determination unit 624. It will be appreciated that non-IR temperature sensors (e.g., an electrical temperature sensor) 624 may be used. In the embodiment of FIG. 6A, TDU 624 is a part of the handpiece 620. In some embodiments, the temperature sensing element, the processor, or the entire TDU 624 may be located outside the handpiece. In preferred embodiments, an IR temperature sensing element is provided as part of the handpiece 620.

Handpiece 620 also includes a plurality of optical elements 634 to sequentially direct laser pulses along a first optical path within the handpiece to a target skin area, and to direct IR energy from the target skin area along a second optical path that is coaxial with and generally counterdirectional to the first optical path for at least a portion of both optical paths. Additional details on embodiments of the optical elements are provided in connection with FIGS. 9A-9F. To facilitate the counterdirectional flow of laser and IR energy, the handpiece comprises a first optical element (not shown) having a first open area through which the first optical path passes, i.e., the laser pulses do not engage the first optical element, and pass through the first open area. In contrast to the laser pulses, however, the IR energy does engage the first optical element, which is preferably a reflective optical element (e.g., a mirror). The first optical element directs the IR energy from the target skin area to the temperature sensing element in TDU 624. The signal from the temperature sensing element is processed to determine skin surface temperature at a desired rate of from 10 to 1 million times per second.

The plurality of optical elements 634 in handpiece 620 also includes at least one second optical element (not shown), and more preferably a plurality of second optical elements, that are engaged by the laser pulses and/or IR energy from the target skin area. In one embodiment, shown in more detail in FIGS. 9A-9F, the at least one second optical element comprises eight (8) optical elements, with the first optical path (i.e., the laser pulse path) engaging all eight optical elements, and the second optical path engaging five of the optical elements in addition to the first optical element. The optical elements may include one or more of lenses (e.g., plano-convex lenses, turning mirrors, meniscus lenses, aspherical lenses, flat lenses, etc.), mirrors (e.g., aspherical mirrors), or other optical elements (e.g., optical parametric oscillators) to direct the laser pulses received from the optical laser source (e.g., via an optical fiber cable) to a target skin area. In preferred embodiments, the at least one second optical element comprises a plurality of lenses (e.g., at least three lenses) and at least one mirror, and the first and second optical paths engage at least two lenses and the last least one mirror. The optical elements 634 may in various embodiments concentrate the laser energy to a single target skin area, or may include beam-splitting elements to split each pulse beam into multiple beams to treat a plurality of target skin areas simultaneously.

In one embodiment (see FIGS. 7, 9C, 9E, 9G), the plurality of optical elements 634 includes a movable scanning mirror capable of movement to direct laser pulses to different target skin areas within a first skin area cooled by cooling window 628. The movable scanning mirror also limits IR energy received by TDU 624 to IR energy from substantially only the target skin area to which the laser is directed at any given time, i.e., it eliminates IR light from other skin areas within the larger first skin area cooled by cooling window 628, which is significantly larger than a single target skin area. In embodiments including a movable scanning mirror, after a first target skin area is treated by one or more laser pulses, the scanning mirror is repositioned to direct subsequent pulses to a new (i.e., second, third, etc.) target skin area within the larger first skin area cooled by the cooling window 628. When a desired number of target skin areas have been treated at a single cooling window position, the user may reposition the cooling window 628 to a new position covering a new skin area, and a different group of target skin areas within the new skin area may be treated by laser 610 using scanner in handpiece 620. In one embodiment, the position of the movable scanning mirror may be adjusted on two or more axes, e.g., by one or more motors, thereby directing succeeding pulses to different target skin areas within the first skin area, enabling treatment of a relatively high proportion of the total area in contact with the cooling window. In alternative embodiments, the plurality of optical elements 634 may not include a scanner.

Referring again to FIG. 6, system 600 further includes a controller 640, which may comprise one or more processing elements such as microprocessors, microcontrollers, field programmable gate arrays (FPGAs), etc. to control the operations of the laser treatment system. Controller 640 includes a pulse timing control unit 642 that controls the timing of the laser pulses from laser 610, including initiating the pulse at a first timepoint and terminating the pulse at a second timepoint. The pulse timing control unit 642 may receive data from temperature sensor 624, and may initiate the therapeutic laser pulse at a first timepoint based on, e.g., a manual signal from a user or a determination that target skin area has been cooled to a desired surface temperature (e.g., 15° C., 10° C., 5° C., 0° C., –5° C., –10° C., etc.). Pulse timing control unit 642 may also terminate the therapeutic laser pulse at a second timepoint based on, e.g., a predetermined pulsewidth or a determination that the surface temperature of the target skin area has reached a threshold surface temperature (e.g., indicating that a deeper target structure such as a sebaceous gland has reached a damage threshold temperature, e.g., 60° C.-75° C.).

Controller 640 also includes a temperature sensing control unit 644 that controls the operation of the TDU 624. Temperature sensing control unit 644 ensures that the TDU 624 determines the surface temperature of a target skin area at a desired (e.g., programmed or predetermined) sampling rate such as 10 or more times per second. Controller 640 may synchronize the operations of the temperature sensing control unit 644 with the pulse timing control unit 642. In one embodiment, the pulse timing control unit 642 and the temperature sensing control unit 644 may comprise one or more of software, firmware, or other programming code operating in the controller 640. In one embodiment, the pulse timing control unit 642 and the temperature sensing control unit 644 may comprise separate processors or subprocessors, and/or separate executable code programs comprising one or more of software, firmware, etc., within controller 640. A wide variety of hardware and software designs may be used to achieve the functions described herein, and all are considered as within the scope of the present disclosure.

Controller 640 may also control other operations within the therapeutic laser treatment system 600 (e.g., software and firmware units and subunits, timers, mechanical or electrical elements or subsystems, etc.). These functions may also include, without limitation, control of the positioning of a movable scanning mirror for determining a target skin area, as discussed above and in greater detail in connection with FIGS. 7 and 9A-9F. Controller 640 also controls the operation of cooling system 622, including without limitation the temperature at which the cooling window is maintained (which may be determined by a user or by the patient's skin type as described in connection with FIG. 6B), the cooling capacity (i.e., the thermal energy removal rate of the TEC), status alarms, etc.

A user interface 650 is preferably provided to allow a system user to select or program one or more parameters (e.g., beam diameter or spot size, fluence, wavelength, target temperature of the surface of the target skin area, cooling temperature of the target skin area at which a pulse may be delivered, etc.) to control the operation of therapeutic laser system 600. User interface 650 may also display various status indicators and data associated with the system and/or a treatment session, such as the current laser parameters, duration of treatment, number of pulses delivered, etc. Controller 640 may also receive and process inputs from the user interface 650, and provide outputs to the user interface. In alternative embodiments, the user interface may be omitted.

Finally, the system 600 includes a power supply 660 for providing power to one or more of the foregoing portions of the system. In one embodiment, power supply 660 may comprise a power supply coupled to a standard NC power outlet to convert AC to DC power at one or more voltages, and may include a battery (e.g., for backup in the event of a power outage), a supercapacitor, etc. Power supply 660 also provides power to controller 640, which in turn includes a current-controlled power supply for driving the laser 610 and/or other system components and subassemblies at rapid switching rates based on inputs from pulse timing control unit 642, temperature sensing control unit 644, cooling system 622, temperature sensor 24, and scanner 634.

Figure 6B:
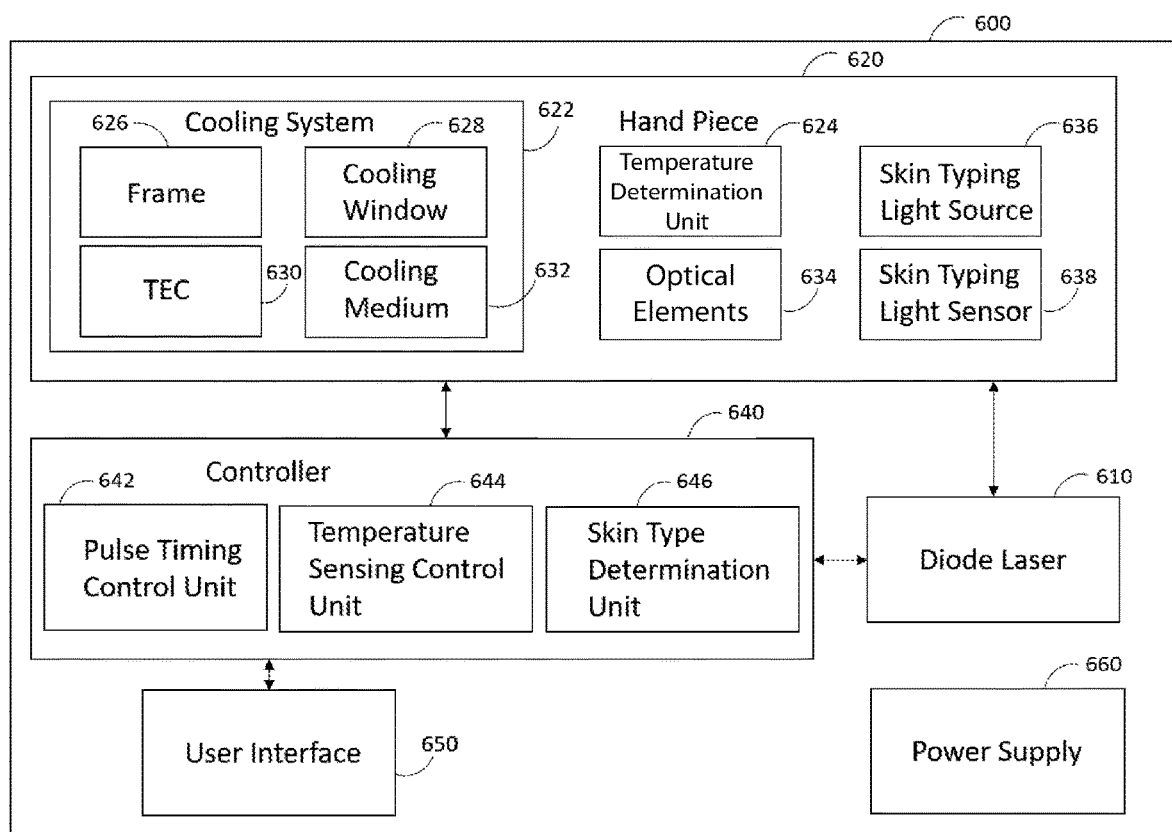

FIG. 6B is a block diagram of an alternative embodiment of therapeutic laser system 600 of FIG. 6A. The therapeutic laser system of FIG. 6B is capable of determining the skin type of a patient, and adjusting one or more treatment parameters based thereon. Like numbers are used for like elements in FIGS. 6A and 6B, and the discussion of FIG. 6B omits or limits previously discussed elements of FIG. 6A for brevity and to avoid repetition. Elements previously described in connection with FIG. 6A will have similar functions in FIG. 6B.

The system of FIG. 6B allows one or more treatment parameters of the system 600 to be adjusted to minimize discomfort and/or pain to patients that may result from differences in skin type. Handpiece 620 includes a skin typing light source 636 for applying a multi-wavelength light signal to determine a skin type of the patient. Although different skin typing systems may be used, in one embodiment the system 600 of FIG. 6B determines a Fitzpatrick skin type of the patient. Skin typing light source 636 may generate noncoherent, multi-wavelength light in one or more of the visible and IR light ranges. A skin typing light sensor 638 is provided to sense a portion of the light from light source 636 that is reflected from the skin of the patient.

Controller 640 includes a skin type determination unit 646 that receives data from the skin typing light sensor 638 relating to, e.g., the absorbance or non-absorbance of the patient's skin of particular wavelengths of light from the skin typing light source 636. The skin type determination unit 646 analyzes the absorbance/non-absorbance data and determines a skin type of the patient. Controller 640 includes logic (e.g., executable software or firmware code, not shown) to modify one or more aspects of the laser treatment based on the patient's skin type to maintaining the skin surface temperature below a desired maximum during treatment.

Without being bound by theory, patients with darker skin (i.e., a higher melanin content than lighter skin) may experience a more rapid temperature rise as relatively more energy from laser pulses is absorbed by the more highly concentrated melanin particles. To avoid an excessive temperature (and an increased risk of patient discomfort/pain), controller 640 may, for example, provide additional cooling (i.e., longer cooling time) for patients with darker skin; lower a target skin temperature at which a therapy pulse is or may be initiated (e.g., automatically initiating therapy or providing a prompt to a user when the skin is cooled to 5° C. for patients with darker skin instead of 10° C. for lighter-skin patients); lower a fluence of the laser pulses to deliver less energy per unit time for darker skin patients; or lower a peak power of the laser pulses of a laser therapy. The controller may also modify or change other parameters such as laser pulse duration and laser spot size to ensure efficacious surface temperature control in the treatment of a wide range of skin types.

FIGS. 6A and 6B illustrate a system according to certain embodiments of the invention involving cooling the skin before, during, and after pulse delivery. Alternative embodiments of the invention include systems with no cooling of the skin, or without cooling of the skin during one or more of the periods before, during, and after delivery of the therapeutic laser pulse. Additional alternative embodiments include systems in which different cooling capacities (i.e., rate of heat removal from the skin) are used in the periods before, during, or after delivery of the laser pulse, and during portions of these periods.

Figure 7:
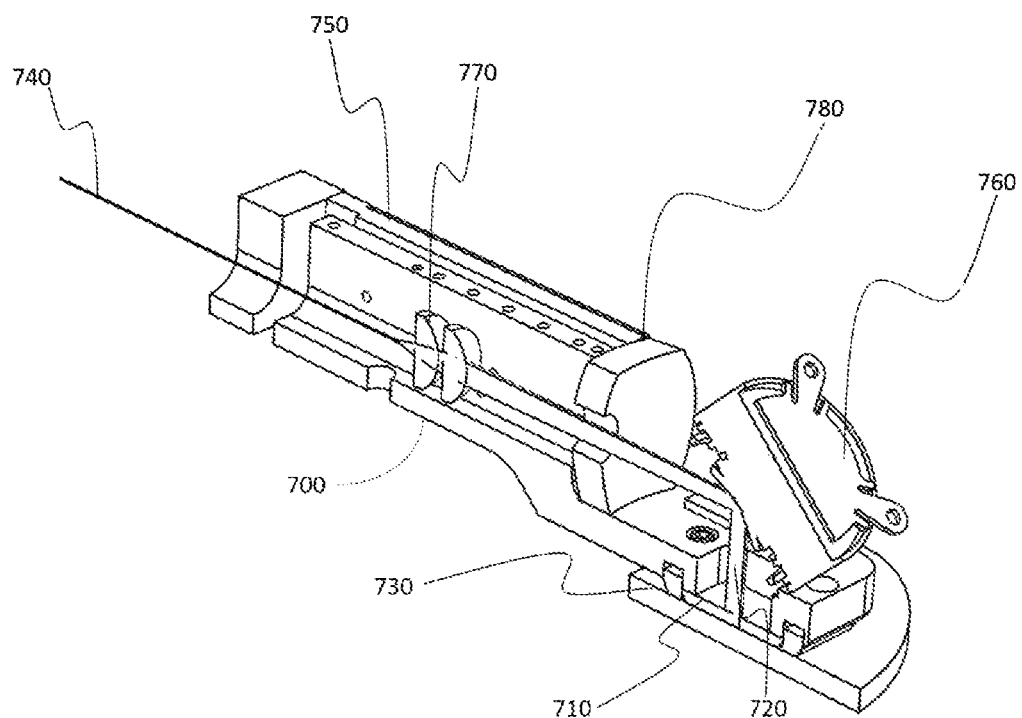
FIGS. 7 and 8 are simplified figures of a handpiece according to an embodiment of the present invention.

FIG. 7 is a simplified sectional view of the interior of one embodiment of a handpiece 700 for cooling a first skin area 730, applying laser pulses to one or more target skin areas within the first skin area, and determining the surface temperature of the target skin area(s). Laser pulses, visually shown as a laser beam 720 at an instant of time, are delivered to the handpiece 700 via an optical fiber 740 from a diode laser (e.g., laser 610 of FIG. 6). After exiting optical fiber 740, pulses 720 pass along a first optical path through focusing lenses 770 and an aperture in a temperature detection mirror 780. Pulses 720 are redirected by a scanning mirror 760, and pass through a cooling window 710 to a target skin area within a first skin area cooled by the cooling window. Scanning mirror 760 may be controllable (e.g., by a motor) and repositionable such that one or more laser pulses 720 are sequentially directed to a series of target skin areas within the cooling window, without moving the cooling window 710 to contact a different area of skin 730. Scanning mirror 760 also receives IR energy traveling from substantially only the target skin area, and excludes IR energy from other (i.e., non-target) areas within the first skin area. The IR energy from the target skin area (not shown) travels along a second optical path generally counterdirectional to the first optical path, and may occur simultaneously with the delivery of a laser pulse.

Handpiece 700 also includes a thermoelectric cooler 750, which includes a heatsink portion (not shown) in contact with cooling window 710 to maintain the cooling window at a desired (e.g., programmed) temperature during contact with the first skin area 730. Cooling window 710 preferably cools the first skin area from a first surface temperature (e.g., body temperature) to a second surface temperature before laser pulses 720 are applied to the skin. In one embodiment, the first skin area is cooled before, during, and after application of a laser pulse thereto.

Skin temperatures may be detected by infrared energy radiated generally counterdirectionally to the laser pulses from the target skin area through the cooling window 710. This infrared energy is reflected by scanning mirror 760 onto temperature detector mirror 780, which focuses the infrared energy on a detection element (not shown), which generates a temperature signal processed by a processor to determine the temperature of the target skin area at a desired sampling rate.

Figure 8:
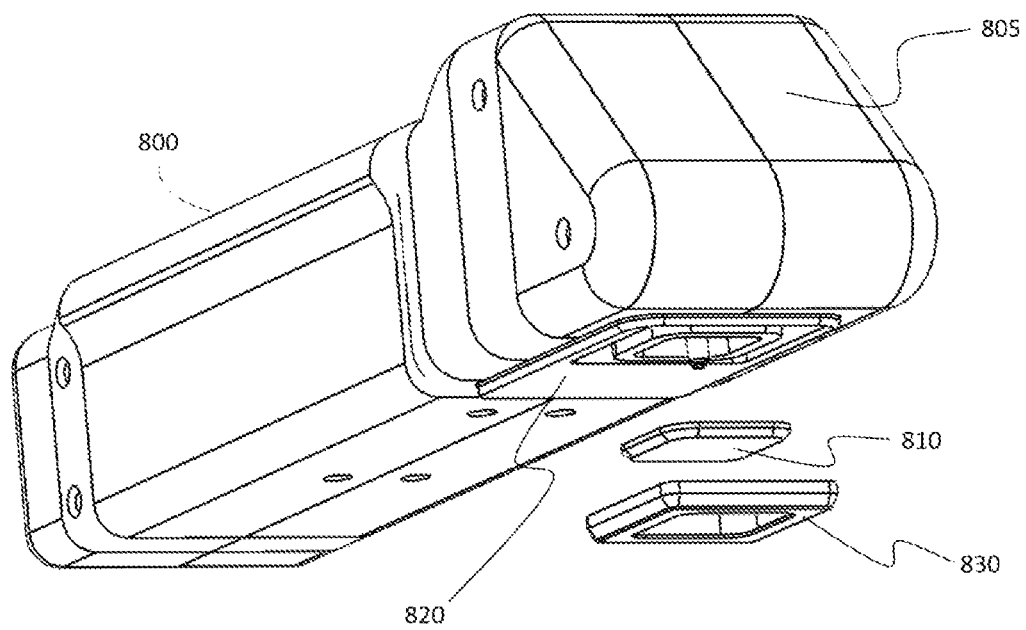

FIG. 8 is a simplified partial exploded, external view of a handpiece 800 for cooling skin and applying laser pulses thereto. In one embodiment, the internal components of FIG. 7 may be enclosed within a housing 805. A cooling window 810 (which may be the same as cooling window 710 of FIG. 7) is maintained in contact with a cooling heatsink 820 (which may be the same as heatsink of TEC 750 of FIG. 7) by a window frame 830, which has no thermal function and merely maintains cooling window 810 in contact with heatsink portion 820. It will be appreciated that additional or alternative components may be included in the handpiece of FIGS. 7 and 8, and that other similar handpiece configurations and geometries may be used to provide a handpiece providing skin cooling and laser pulse delivery along a first optical path as well as skin temperature determination and monitoring by IR energy traveling along a second optical path generally counterdirectional to the first optical path.

FIGS. 9A-9F are perspective (9A, 9B), optical schematic (9D, 9F), and exploded (9C, 9E, 9G) views, respectively, of one embodiment of a handpiece 900 for providing laser therapy to a patient's skin as part of a laser treatment system. The handpiece 900 provides contact cooling of the skin, and senses skin temperature from IR energy emitted by the skin along a second optical path that is at least partially coaxial with the first optical path traveled by the laser pulses. By sensing temperature along an optical path that is partially coaxial with the laser pulse path, greater accuracy is achieved in sensing the temperature of only the target skin area—i.e., the skin actually receiving the energy of a laser pulse—as opposed to adjacent tissues not receiving laser energy. This is achieved by sensing IR energy from the skin through the contact cooling window, and by using optical elements that limit the IR energy received by the temperature sensor (and used to determine skin temperature) to substantially only IR energy emitted by the target skin area. Because the temperature determination is based only on IR energy emitted from the target tissue actually receiving the laser pulses, and not on IR energy emitted from adjacent non-target tissue that does not receive laser pulse energy, the temperature of the target skin area is obtained with high accuracy.

Figure 9A:
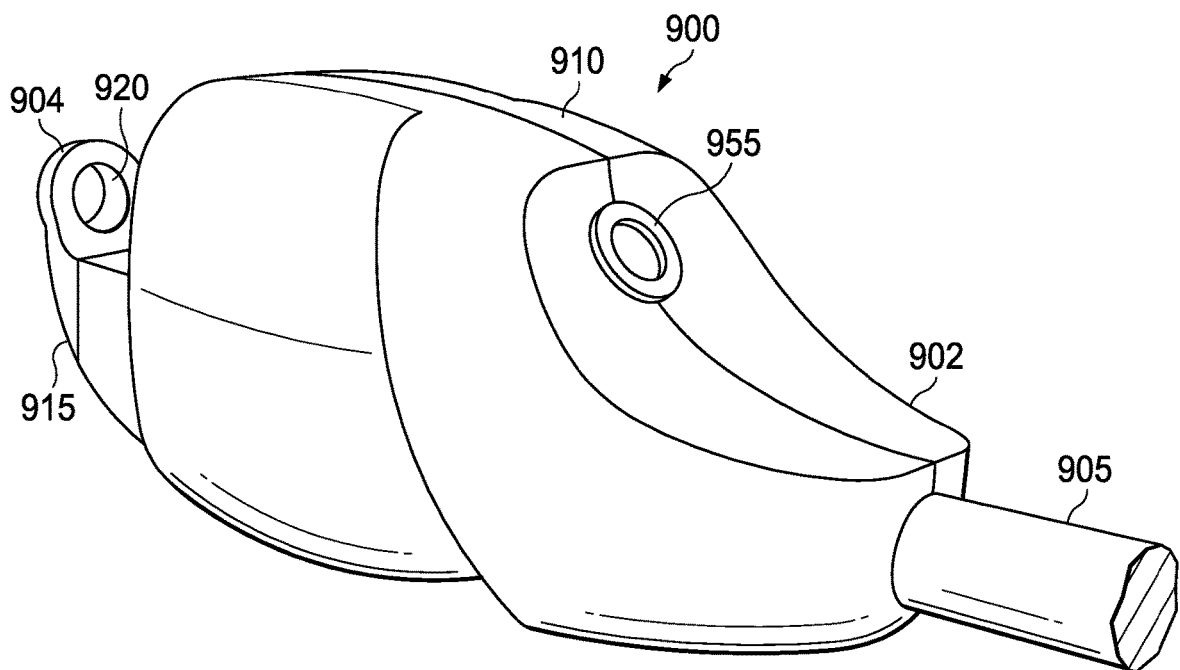
FIGS. 9A and 9B are perspective views of a handpiece according to an embodiment of the present invention.
Figure 9B:
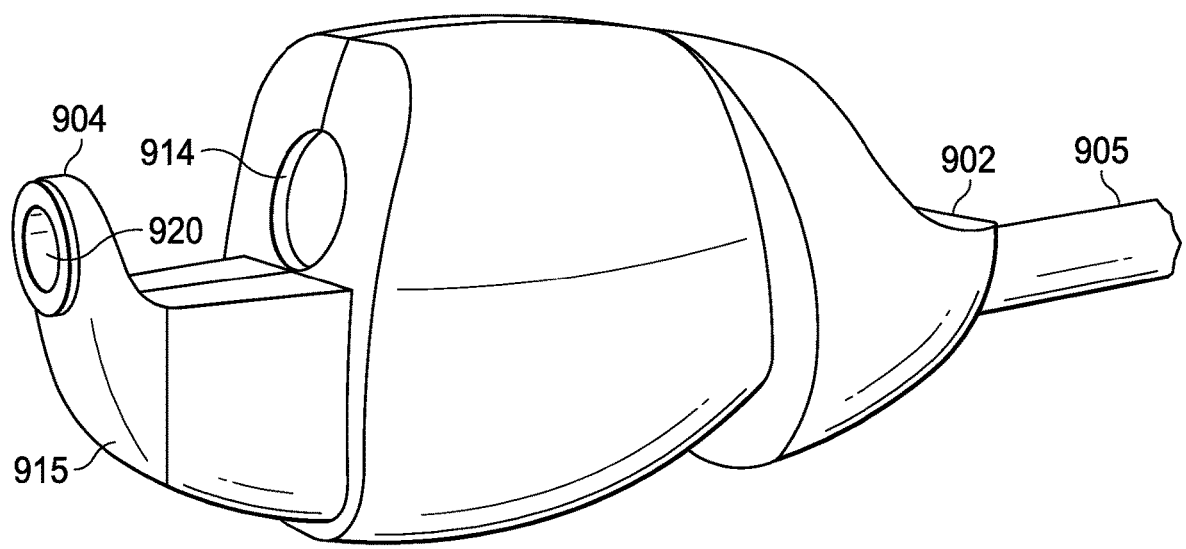

FIGS. 9A and 9B are perspective views of the handpiece 900, which includes a proximal end 902 and a distal end 904, and comprises a housing 910 having a shape adapted for holding by a user (e.g., a physician or technician), and having an inner volume shielding a plurality of optical elements, discussed more fully below in connection with FIGS. 9C, 9E, and 9G). An optical cable 905, which comprises an optical fiber core (not shown), is coupled to the proximal end 902 of the handpiece 900. Optical cable 905 is coupled to a laser source (not shown) which generates and delivers laser pulses to the handpiece 900 through the cable. Optical cable 905, and specifically the optical fiber therein, terminates inside the proximal end 902 of handpiece 900 in a standard optical coupler 907 (FIGS. 9C, 9E, and 9G) such as an SMA coupler, although other standard optical couplings may be used.

At the distal end 904 of the handpiece 900, a contact cooling unit 915 includes a cooling window 920 to cool, by direct contact, a first skin area equal in size to the cooling window. In addition to the cooling window 920, contact cooling unit 915 also comprises other elements more fully shown in FIG. 9C, including a cooling window heat sink 916 that surrounds the cooling window 920, a thermoelectric cooler (TEC) 917, and a second heat sink 918. Laser pulses from optical cable 905 pass through handpiece 900 along a first optical path and are applied to a target skin area, which comprises a smaller skin area within the first skin area cooled by the cooling window.

As shown in FIG. 9B, housing 910 of handpiece 900 includes an optical aperture or port 914 through which laser pulses exit the housing and travel along the first optical path through the cooling window 920 to the target skin area. Cooling window 920 is spaced a desired distance from housing 910 by cooling unit 915, which also functions as a spacing member to allow a user to visualize the area being cooled and treated by the handpiece 900.

Figure 9C:
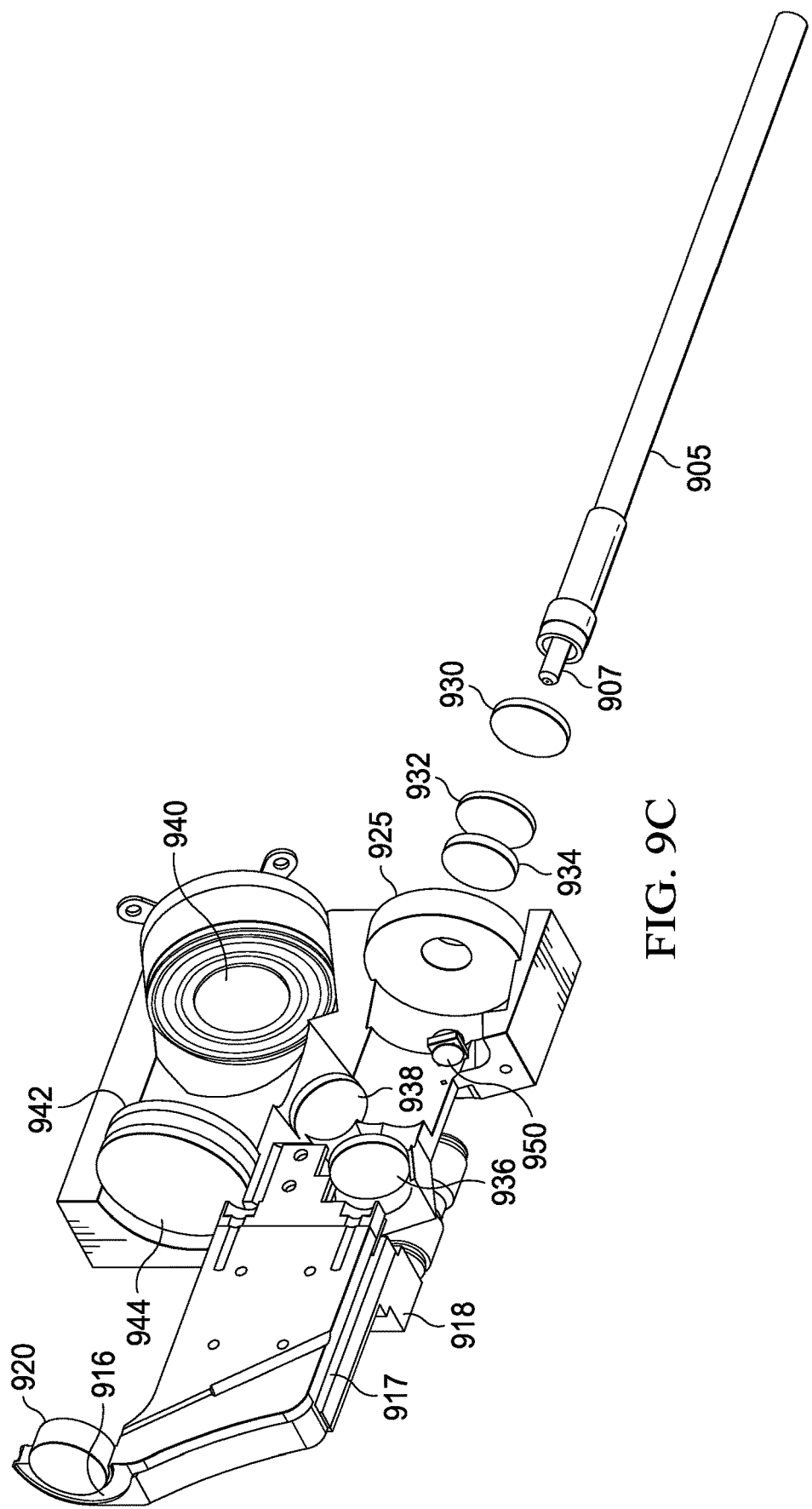
FIGS. 9C, 9E, and 9G are partially exploded views of the handpiece of FIGS. 9A and 9B.

FIG. 9C is a partially exploded view of the interior portion of handpiece 900 with housing 910 removed, showing in greater detail the optical elements, contact cooling unit, and temperature determination unit included in the handpiece 900. In alternative embodiments, the temperature determination unit may be separate from the handpiece 900. The handpiece 900 includes a plurality of optical elements 925, 930, 923, 934, 936, 938, 940, 942, and 944 within the housing 910, although in alternate embodiments one or more optical elements by be located outside the housing. Different combinations of these optical elements each define the first optical path taken by laser pulses 908 to the target skin area (FIG. 9D) and the second optical path taken by the IR energy from the target skin area to a temperature sensing element 950 (FIG. 9E).

FIG. 9C also shows additional details of contact cooling unit 915, which includes a cooling window heatsink 916 surrounding the cooing window 920. Heat is removed from the skin by direct contact between the first skin area and the cooling window 920, and is passed to the heatsink 918, which is coupled to the cool side of a TEC 917 to maintain the cooling window 920 at a desired temperature (e.g., a user selectable temperature in the range of −10° C. to 25° C.). TEC 917 passes heat received on its cool side from cooling window 920 via cooling window heatsink 916 to its hot side, and is removed from the TEC hot side by a second heatsink 918, which is coupled to a circulating cooling medium (not shown) such as water.

The handpiece 900 of FIG. 9C includes a temperature determination unit, which may be a temperature determination unit 624 as shown in FIG. 6. Although the temperature determination unit of FIGS. 6 and 9C is part of handpiece 900, in alternative embodiments, all or portions of the temperature determination unit may be located outside of handpiece 900. Referring again to FIG. 9C, handpiece 900 includes a temperature sensing element 950 for receiving IR energy emitted from the target skin area through the contact window 920 along a second optical path generally counter-directional to the first optical path taken by laser pulses 908. The first and second optical paths share a common optical axis for at least a portion of their lengths. In response to receiving IR energy from the target skin area, temperature determination unit determines the surface temperature of the target skin area one or more times before, during, or after the application of the at least one therapeutic laser pulses. Temperature sensing element 950 generates a signal indicative of the temperature of the target skin area, and is coupled to a processor (not shown) which receives and processes the signal to determine the surface temperature of the target skin area at a desired rate (e.g., 10-1 million times per second). The temperature determination unit that may determine or measure surface temperature of the target skin area before during, or after treatment with laser pulses 908. Operation of the temperature determination unit may be controlled by a temperature sensing control unit 644 (FIG. 6).

Figure 9D:
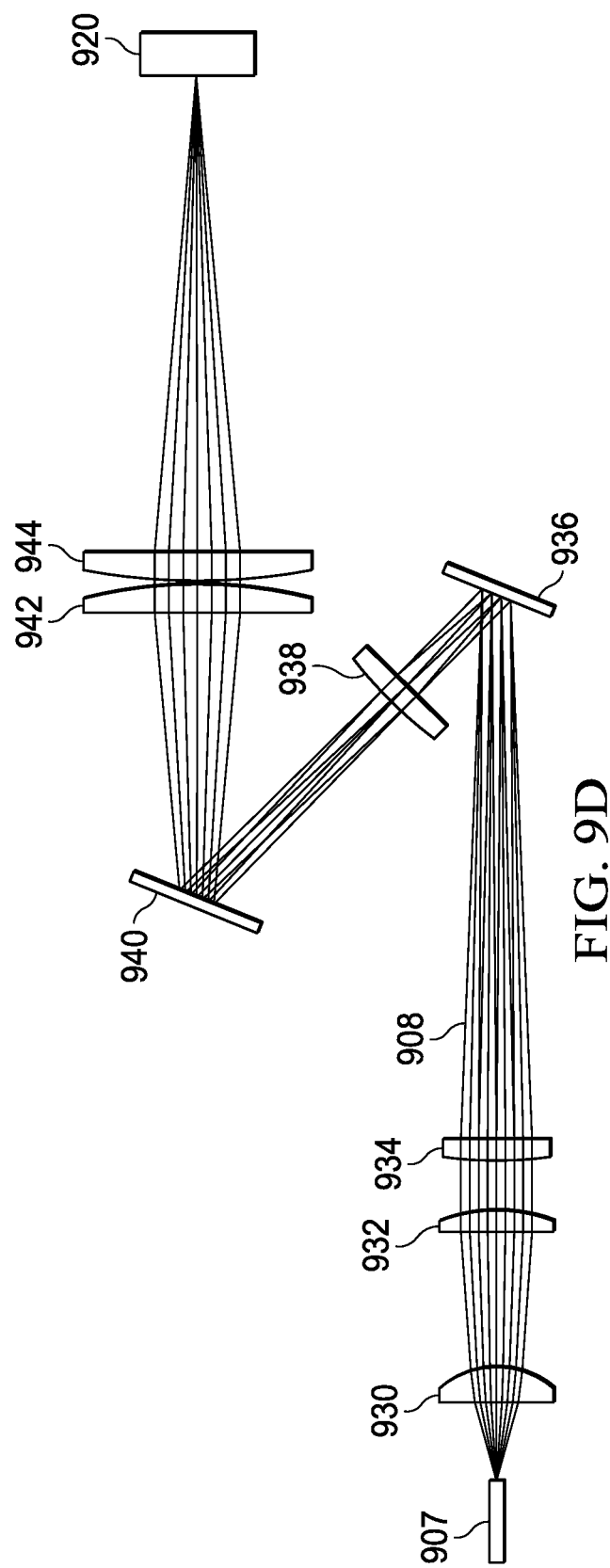
FIGS. 9D and 9F are optical schematics showing optical paths in the handpiece of FIGS. 9A and 9B.

FIG. 9D is an optical schematic showing the optical path taken by the laser pulses 908 in passing through the handpiece to the target skin area, and the optical elements that the laser pulses engage (e.g., lenses through which a laser pulse passes or mirrors reflecting the pulses). FIG. 9D shows a laser pulse beam 908 exiting the optical fiber coupling 907 and passing through three plano-convex lenses 930, 932, 934 before being reflected by a turning mirror 936. Plano-convex lenses 930, 932, 934 in the embodiment of FIG. 9D comprising BK7, fused silica lenses, although many different lens types may be used. In an alternative embodiment, lenses 930, 932, and 934 may be replaced by a single aspherical lens (not shown). Although fixed in position in the embodiment of FIG. 9D, turning mirror 936 in alternative embodiments may comprise a steerable mirror that is adjustable to change the angle of reflection.

After the laser pulse beam 908 is reflected by turning mirror 936, it passes through another plano-convex lens 938 and is reflected by a beam steering element comprising a movable turning mirror 940 that is movable or adjustable on two axes by motors, also known as a "scanning mirror." By moving the position of the mirror, succeeding pulses may be directed to different target skin areas within the first skin area cooled by the cooling window 920. In alternative embodiments, beam steering elements different from or in addition to the movable turning mirror 940 may be used. Plano-convex lens 938 is made of ZnSe in one embodiment, although other materials may be used in different embodiments. Movable turning mirror 940 reflects the laser pulse beam 908 through a meniscus lens 942 and a plano-convex lens 944 before passing through cooling window 920. Meniscus lens 942 and plano-convex lens 944 comprise ZnSe in one embodiment, but may be made of different materials in alternative embodiments. In a further alternative embodiment, lenses 938, 942, and 944 together may be replaced by a single aspherical lens (not shown). Cooling window 920 is made of a material that is transmissive to both laser light at the wavelength(s) output by the laser source as well as IR light emitted from the target skin area. In one embodiment, cooling window 920 is made of sapphire. In alternative embodiments, ZnS, diamond, or ZnSe may be used successive.

Figure 9E:
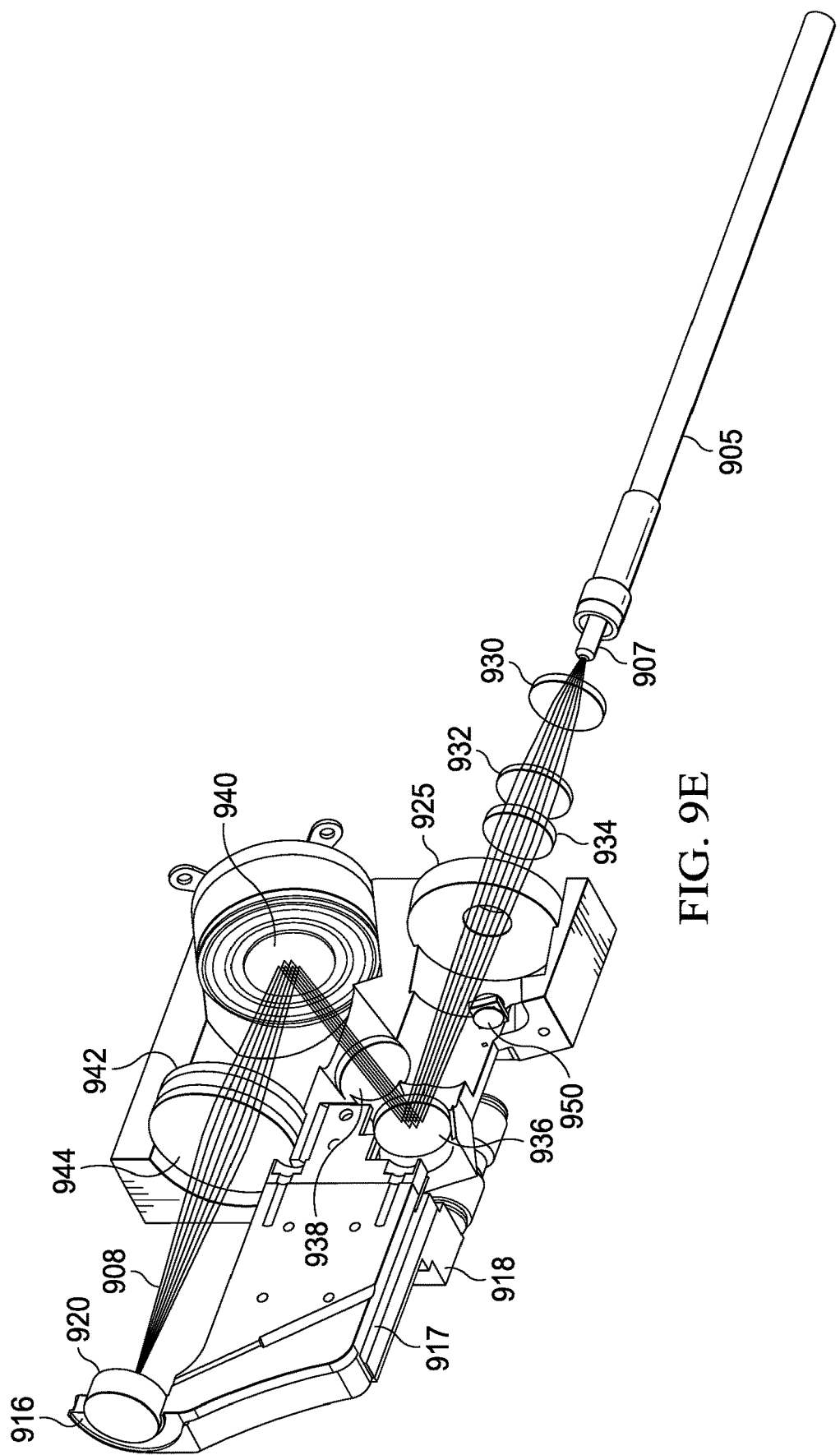

FIG. 9E is the partially exploded view of the interior portion of handpiece 900 shown in FIG. 9C, but includes added lines showing an exemplary laser pulse 908 to illustrate the first optical path traveled by such a pulse. For brevity, discussion of the optical elements already noted in FIG. 9C is omitted. As can be seen, the laser pulse 908 initially follow a path having a linear optical axis from optical coupler 907 to the turning mirror 936. Turning mirror 936 redirects the laser pulse along a different linear optical axis to movable turning mirror 940, which again redirects the laser pulse along a final optical axis to the target skin area cooled by the cooling window 920.

Figure 9F:
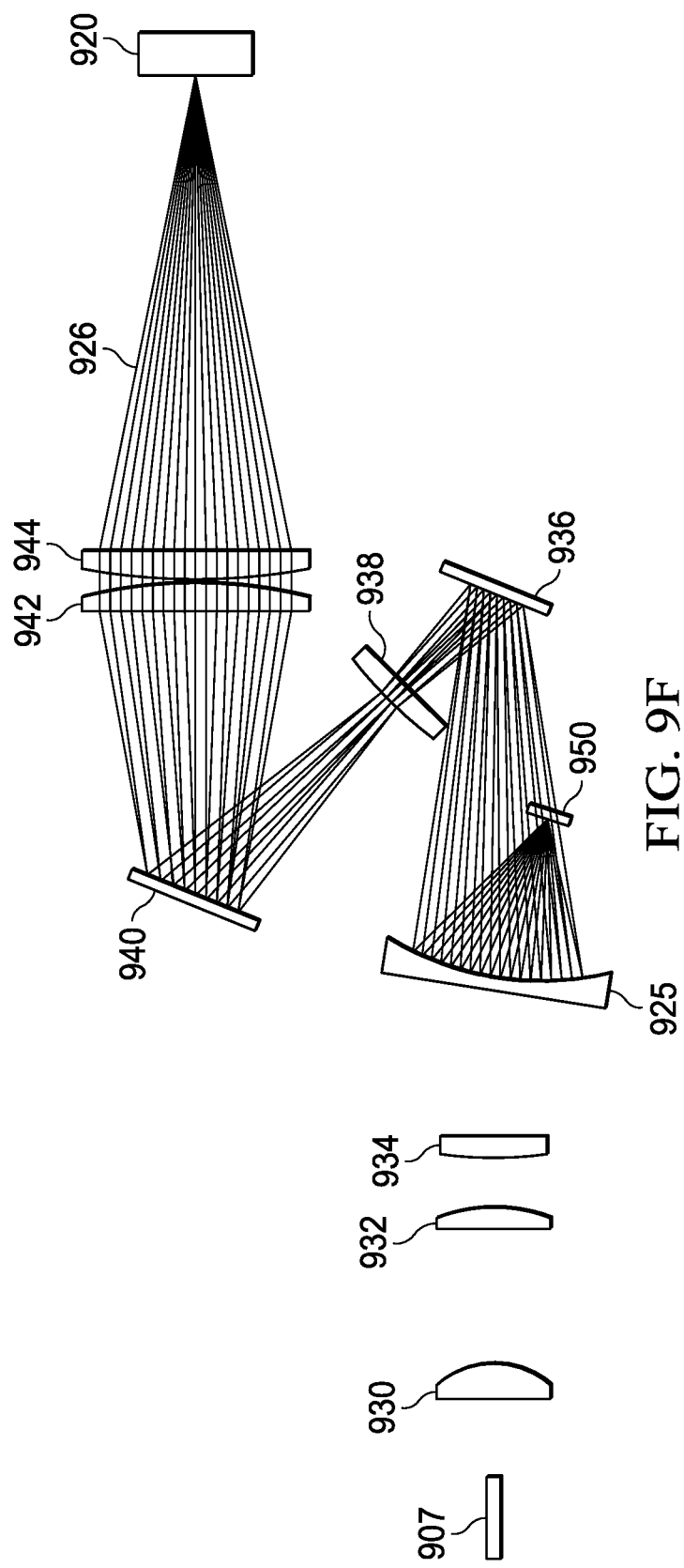

FIG. 9F is an optical schematic showing the optical path taken by infrared (IR) energy 920 emitted from a target skin area and traveling along a second optical path, and in particular the optical elements engaged by the IR energy in passing through the handpiece 900 to the temperature sensing element 950. As previously noted, the second optical path is generally opposite to the direction of the first optical path, and is coaxial with the first optical path for at least a portion of the length of both paths. Because the target skin area is within the first skin area and in contact with cooling window 920, FIG. 9F shows IR energy 926 emitted from the skin directly through cooling window 920. As noted in connection with FIG. 9D, cooling window 920 is transmissive to the IR energy and is made of sapphire in the embodiment of FIGS. 9A-9F. Passing through cooling window 920, the IR energy 926 passes through plano-convex lens 944 and meniscus lens 942 and is then reflected by movable turning mirror ("scanning mirror") 940. The scanning mirror 940 may comprise any of a number of commercially available movable turning mirrors, such as a model MR-15-30 mirror available from Optotune Switzerland AG, Dietikon, Switzerland. In a given position, movable turning mirror 940 directs the laser pulses 908 to the target skin area (and not, e.g., adjacent tissue), and also reflects IR energy 926 emitted in the opposite direction from substantially only the target skin area. IR energy 926 reflected from scanning mirror 940 passes through plano-convex lens 938 before being reflected by turning mirror 936. Convex lens 944, meniscus lens 942, movable turning mirror 940, plano-convex lens 936, and turning mirror 936 are as described in connection with FIG. 9D, and for brevity further discussion is omitted here.

After reflection from turning mirror 936, IR energy 926 is reflected by a first optical element comprising a concentric mirror 925 onto the temperature sensing element 950. Concentric mirror 925 includes an open area (e.g., an aperture or slot) through which the laser pulses 908 pass without engaging the concentric mirror 925. From cooling window 920 to concentric mirror 295, the second optical path taken by IR energy 926 is generally opposite to—but coaxial with—the first optical path taken by laser pulses 908. As noted, highly accurate temperature measurements are made possible by sensing IR energy 926 traveling opposite to but coaxial with the laser pulses 908, because it enables the temperature sensing element 950 to sense IR energy from substantially only the target skin area (i.e., the same skin area receiving the laser pulse energy). However, it will be appreciated that the second optical path taken by the IR energy must eventually be diverted to a non-coaxial path from the first optical path to reach the temperature sensing element 950, which cannot be located in the first optical path without blocking the laser pulses 908. By including a concentric mirror 925 having an aperture, handpiece 900 allows the laser pulses 908 to pass through the concentric mirror but also allows IR energy 926 to travel along second optical path that is initially coaxial with first optical path until being reflected off-axis to the first optical path onto the temperature sensing element 950. Temperature sensing element 950 may comprise any of a number of commercially available infrared sensors, such as a model P13243-013CA-SPL sensor available from Hamamatsu Corp., Bridgewater, NJ In a preferred embodiment, temperature sensing element 950 includes an optical filter (e.g., a substrate transparent to the IR radiation from the target skin area with an optical coating) such that the temperature sensing element reflects the wavelength(s) of the laser source but transmits the IR energy radiated from the target skin area.

Figure 9G:
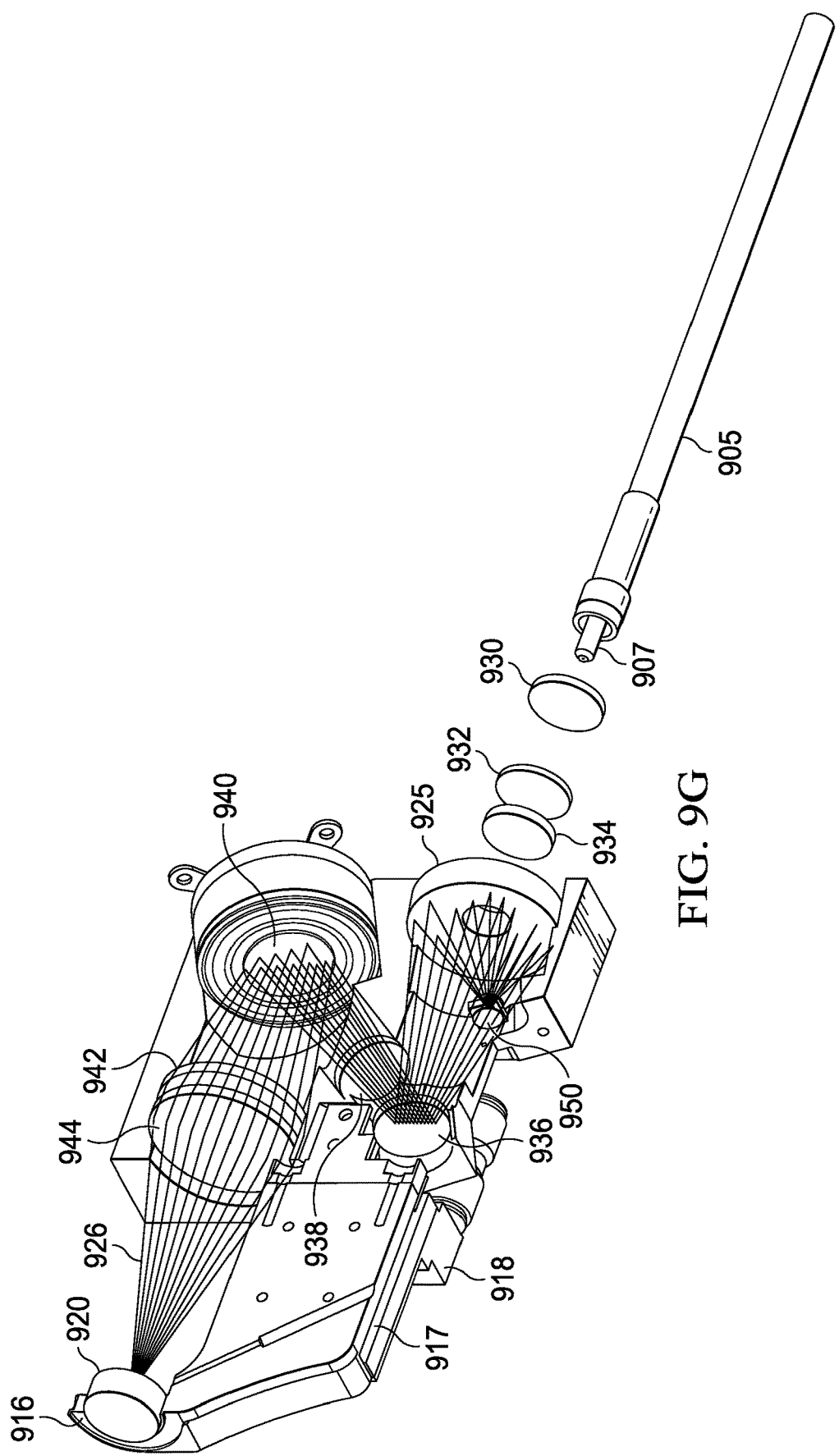

FIG. 9G is the partially exploded view of the interior portion of handpiece 900 shown in FIG. 9C, but includes added lines showing the path taken by IR energy 926 emitted from the target skin area to illustrate the second optical path traveled by the IR energy to the temperature sensing element 950. Further discussion of the optical elements already noted in FIG. 9C is omitted. FIG. 9G depicts IR energy 926 emitted from the target skin area directly through the cooling window 905, initially following a path having a linear optical axis from the target skin area to movable turning mirror 940, which reflects the IR energy 926 along a different optical axis to turning mirror 936. Turning mirror 936 again reflects the IR energy 926 along a different optical axis to the concentric mirror 925, which reflects the IR energy onto the temperature sensing element 950. A processor (not shown) processes the signal from temperature sensing element 950 to determine the surface skin temperature at a desire rate. The processor may be provided either as part of handpiece 900 or may be coupled by wire or wireless connection to temperature sensing element 950. In preferred embodiments, temperature sensing element 950 and the processor associated with it are including in the housing 910, while in alternate embodiments one or both may be located outside the housing or separate from handpiece 910

Figure 10A:
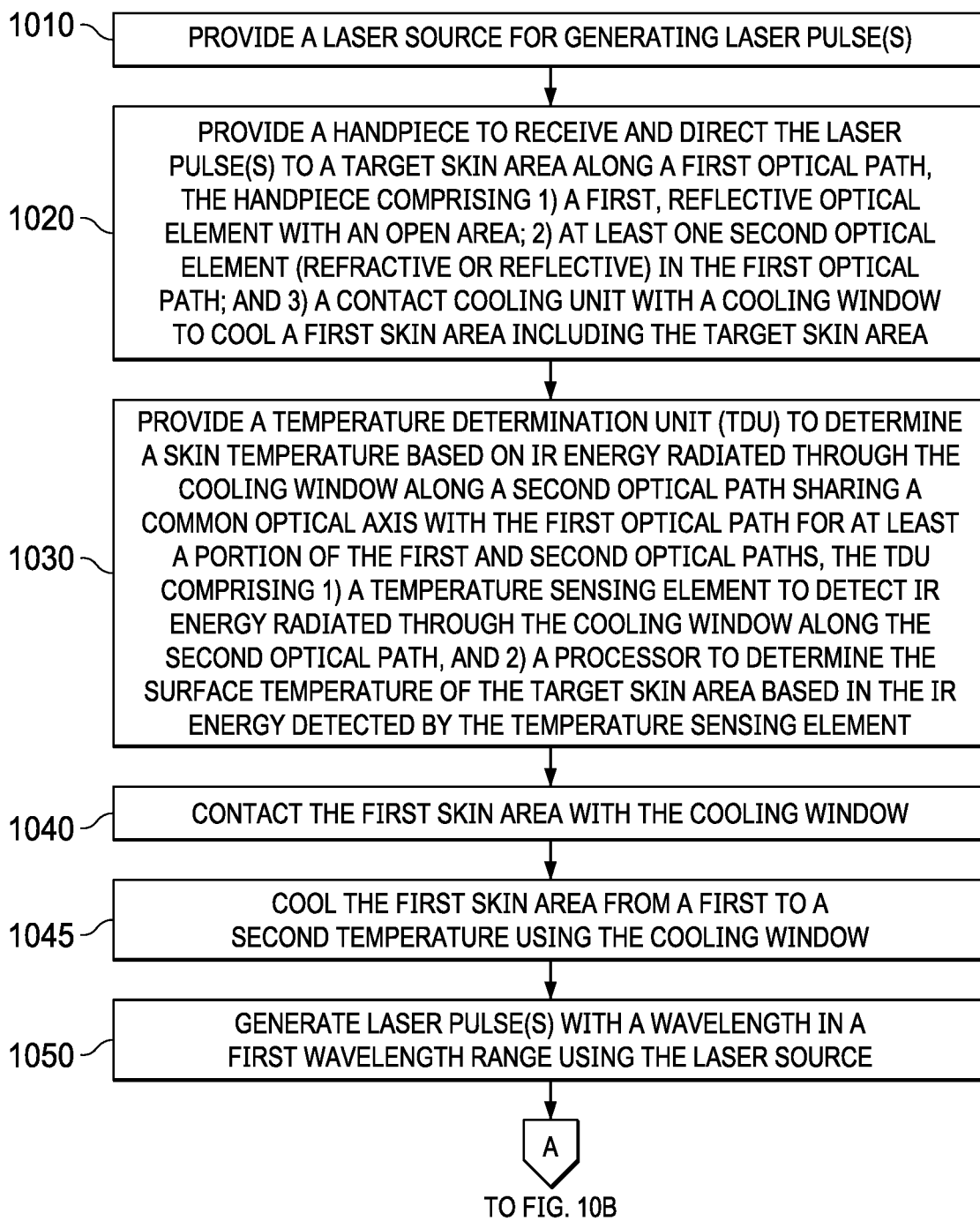
FIGS. 10A and 10B together provide a flowchart illustrating a treatment method according to one embodiment of the present invention.
Figure 10B:
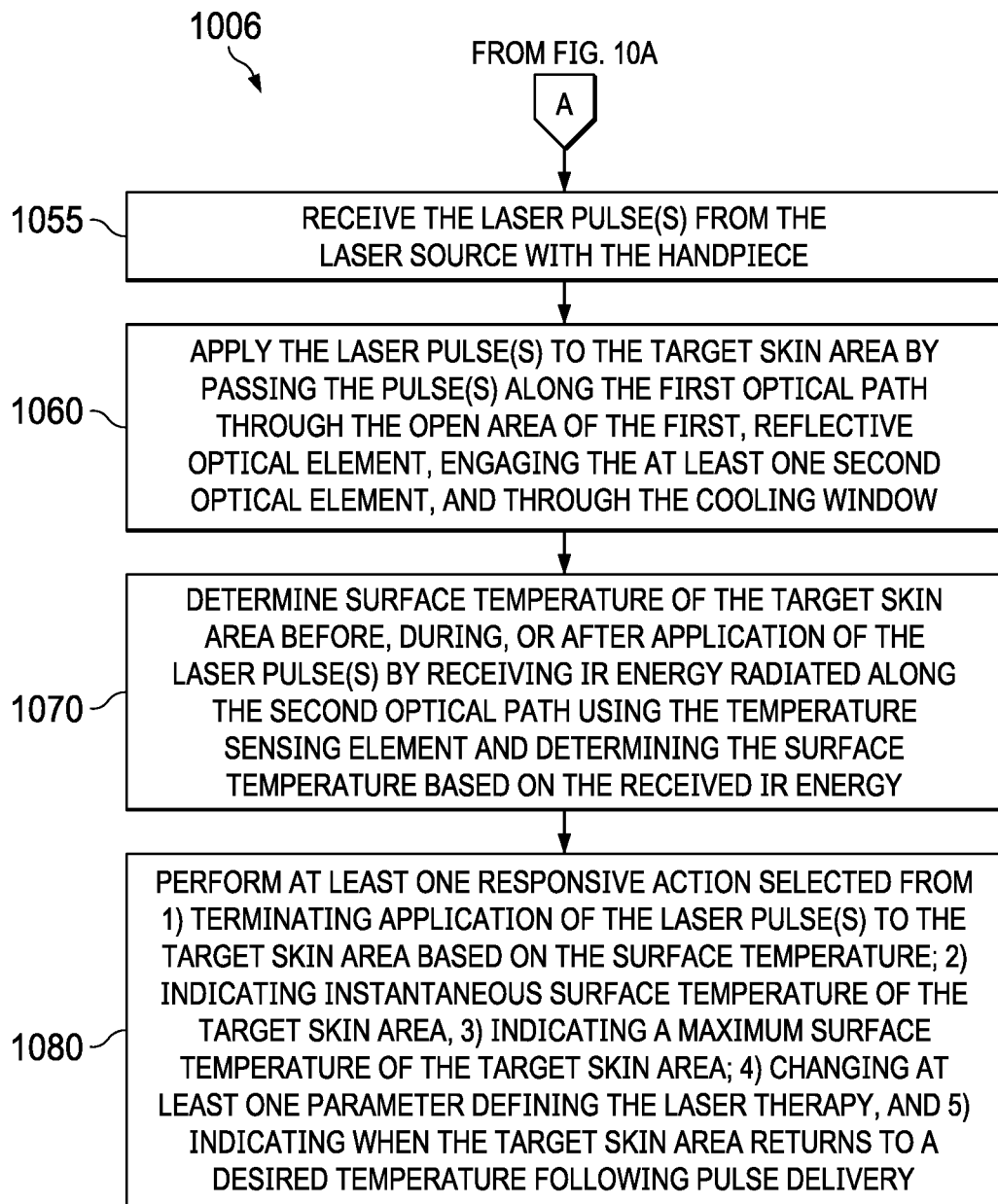

FIGS. 10A and 10B together disclose one embodiment of a method 1006 of treating the skin of a patient with one or more therapeutic laser pulses according to the present disclosure, with FIG. 10A depicting steps 1010-1050 and FIG. 10B depicting steps 1055-1080. The method involves the use of one embodiment of a laser system as described in connection with FIGS. 9A-9F. The method includes providing a laser source for generating one or more laser pulses as a laser therapy (1010), as shown in FIG. 10A. In one embodiment, the laser source comprises a semiconductor laser having a wavelength in one of the near-infrared spectrum and the short-wavelength IR spectrum.

The method also includes the step of providing a handpiece coupled to the laser source to receive at least one therapeutic laser pulse from the laser source, and to direct the pulses along a first optical path to a target skin area (1020). The handpiece includes a first optical element, at least one second optical element, and a contact cooling unit. The first optical element includes a first open area comprising one of an aperture and a slot through which the first optical path passes. In one embodiment, the first optical element may comprise concentric mirror 925 of FIG. 9C. The at least one second optical element comprises one of a refracting element (e.g., a lens), and a reflective element (e.g., a mirror), and may include multiple lenses and mirrors similar to handpiece 900 in FIG. 9C. The contact cooling unit comprises a cooling window for contacting and cooling a first skin area of the patient by direct contact. The first skin area includes a target skin area to be treated by the at least one therapeutic laser pulse (i.e., the target skin area is the skin that actually receives the energy of one or more therapeutic laser pulses). The cooling window is made of a thermally conductive material that is transmissive to infrared energy and laser light at a first wavelength range that includes the wavelength of the laser source.

Referring again to FIG. 10A, the method includes the step of providing a temperature determination unit (TDU) to determine a surface temperature of the target skin area based on IR energy radiated from the target skin area through the cooling window (1030). The IR energy radiates along a second optical path that shares a common optical axis with the first optical path for at least a portion of the first and second optical paths. The second optical path is preferably generally counterdirectional to the first optical path for at least a portion of the first and second optical paths, such that the IR energy for determining skin temperature propagates in the opposite direction to the direction of the laser pulse(s) for at least a portion of the second optical path. The TDU comprises a temperature sensing element that detects IR energy radiated through the cooling window along the second optical path, and a processor that determines the surface temperature of the target skin area based on the IR energy detected by the temperature sensing element. In one embodiment, the temperature sensing element may be the temperature sensing element 950 of FIG. 9C, which provides a continuous or intermittent signal that is processed at a desired rate by the processor to determine the surface temperature of the target skin area at a desired rate (e.g., 10-1,000,000 times per second, or a sampling interval of 100 msec or less). In some embodiments, the temperature determinations may comprise real-time temperature measurements used by a processor to control the duration of the laser therapy.

The method also includes the step of contacting the first skin area with the cooling window (1040). This may be done by a handpiece user (e.g., a physician or technician) bringing the cooling window into contact with a skin area to be treated, which cools the first skin area in contact with the cooling window from a first temperature to a second temperature (1045). The method further includes the step of generating, using the laser source, at least one therapeutic laser pulse having a wavelength within the first wavelength range (1050), shown in FIG. 10A. The method continues in FIG. 10B, with the step of receiving the at least one therapeutic laser pulse with the handpiece (1055). The method also includes the step of applying the at least one therapeutic laser pulse to the target skin area by passing the pulse along the first optical path through the first open area of the first optical element, engaging the at least a second optical element, and through the cooling window into the target skin area (1060).

The method also includes determining the surface temperature of the target skin area one or more times before, during, or after the application of the at least one therapeutic laser pulse (1070). As part of this step, the temperature sensing element receives IR energy radiated from the target skin area along the second optical path, with the IR energy engaging the at least a second optical element and being reflected by the first optical element onto the temperature sensing element. The processor determines the surface temperature of the target skin area based on the infrared energy received by the temperature sensing element.

In some embodiments, the TDU may determine the surface temperature of the target skin area a plurality of times before, during, or after the application of the at least one therapeutic laser pulse. As a nonlimiting example, the TDU may initiate determining the surface temperature of the target skin area when the contact cooling window contacts the skin of the patient, and may determine the surface temperature of the target skin area once every millisecond as the skin is cooled, during the application of one or more therapeutic laser pulses to the target skin area, and after the termination of the pulses until the target skin area is cooled to a desired final temperature. In another nonlimiting example, the TDU may determine the temperature of the target skin area at least one time during the delivery of a therapeutic laser pulse, and at least one time before or after the pulse. In preferred embodiments, the temperature sensing element receives IR energy radiated substantially only from the target skin area, and the TDU determines the surface temperature based only on this IR energy.

Finally, the method includes performing at least one responsive action in response to determining the surface temperature of the target skin area (1080). The responsive action may include one or more actions selected from a list of responsive actions. These may include, e.g., terminating the application of the at least one therapeutic laser pulse to the target skin area (i.e., terminating a single pulse or a sequence of pulses), indicating (e.g., via a user interface or display) the instantaneous surface temperature of the target skin area, indicating a maximum surface temperature of the target skin area (e.g., displaying the maximum temperature reached during delivery of one or more pulses), changing at least one parameter of the laser therapy (e.g., reducing or increasing the intensity or duration of therapeutic laser pulses), and indicating when the surface temperature of the target skin area returns to a desired temperature following delivery of one or more therapeutic laser pulses to the target skin area.

In some embodiments, step of providing a handpiece includes providing a handpiece in which the at least a second optical element includes a mirror movable in at least two axes to direct the at least one therapeutic laser pulse to one or more desired target skin areas within the first skin area. The mirror may be the movable turning mirror 940 described in FIG. 9C. In one embodiment, after one or more first therapeutic laser pulses are applied to a first target skin area with the mirror in a first position, the mirror may be moved to a second position, and the method may comprise delivering subsequent laser pulse(s) to a second target skin area different from the first target skin area, but still within the first target skin area cooled by the cooling window. In this case, the laser pulse(s) again pass along a first optical path through the first open area, engage the mirror in the second position, and pass through the cooling window to the second target skin areas. When the pulses are delivered to the second target skin area, the method may also comprise determining the temperature of the second target skin area one or more times before, during, or after the delivery of the laser pulse(s) to the second target skin area by receiving IR energy radiating from the second target skin area along the second optical path, engaging the mirror in the second position, and reflecting from the first optical element onto the temperature sensing element. As previously noted, the first and second optical axes are coaxial for at least a portion of the first and second optical paths. In a preferred embodiment, the first and second optical paths share a common optical axis for at least the portion of the first and second optical axes from the movable mirror to the cooling window.

In some embodiments, the step of providing a handpiece includes providing a handpiece in which the at least a second optical element includes a plurality of lenses and at least one mirror, and the first and second optical paths engage at least two of the plurality of lenses and the at least one mirror. In some embodiments, providing a handpiece in which the at least a second optical element incudes at least four lenses and at least one mirror.

In some embodiments, the steps of generating at least one laser pulse, receiving the at least one pulse with the handpiece and applying it to the target skin area are repeated until the determined surface temperature of the target skin area reaches a target treatment temperature. In some embodiments, determining the surface temperature of the target skin area comprises repeatedly determining the target skin area a plurality of times during the application of a therapeutic laser pulse, and the method further comprises terminating the application of the laser pulse when the surface temperature of the target skin area reaches a target treatment temperature.

In various embodiments, the present invention relates to the subject matter of the following numbered paragraphs.

101. A system for treating the skin of a patient with one or more therapeutic laser pulses, the system comprising:
   a) a laser source adapted to generate at least one therapeutic laser pulse for application to a target skin area;
   b) a handpiece optically coupled to the optical source to receive the at least one therapeutic laser pulse from the laser source and to direct the at least one therapeutic laser pulse to the target skin area along a first optical path, the handpiece comprising:
      1) a first optical element comprising a reflective element and having a first open area through which said first optical path passes, wherein the first open area comprises one of an aperture and a slot;
      2) at least a second optical element comprising at least one of a refractive element and a reflective element, wherein the first optical path engages the at least a second optical element;
   c) a temperature determination unit for determining a surface temperature of the target skin area based on infrared energy radiated from the target skin area through the cooling window along a second optical path sharing a common optical axis with the first optical path for at least a portion of the first and second optical paths, the temperature determination unit comprising:
      1) a temperature sensing element for sensing infrared energy radiated through the cooling window along the second optical path, the temperature sensing element generating a first signal indicative of the infrared energy radiating along the second optical path, wherein the infrared energy radiating along the second optical path engages the at least a second optical element and is reflected by the first optical element to be detected by the temperature sensing element; and
      2) a processor adapted to determine the surface temperature of the target skin area at one or more timepoints before, during, or after the application of one or more of therapeutic laser pulses based on the infrared energy detected by the temperature sensing element.

102. The system of paragraph 101, wherein the handpiece further comprises:
   3) a contact cooling unit comprising a cooling window adapted to contact and cool a first skin area of the patient from a first temperature to a second temperature, wherein the cooling window comprises a thermally conductive material that is transmissive to infrared energy and the laser pulses, the first optical path passes through the cooling window, and the target skin area comprises a fraction of the first skin area.

104. The system of paragraph 101, wherein the first optical element comprises a mirror, and the at least a second optical element comprises at least one lens and at least one mirror.

201. A method for treating the skin of a patient with one or more therapeutic laser pulses, comprising:
   a) providing a handpiece having
      1) a first end for receiving at least one therapeutic laser pulse from a laser source;
      2) a first mirror having an open area comprising one of an aperture and a slot;
      3) at least one second optical element;
      4) a skin contact element at a second end of the handpiece; and
      5) a temperature sensing element adapted to detect infrared energy radiated through the cooling window;
   b) contacting the first skin area with the skin contact element;
   c) receiving at least one therapeutic laser pulse from a laser source at the first end;
   e) applying the at least one therapeutic laser pulse to a target skin area within the first skin area by directing the laser pulse along a first optical path within the handpiece, the first optical path passing through the open area of the first mirror, engaging the at least one second optical element, and passing through the cooling window to the target skin area;
   f) sensing infrared energy radiated from the target skin area along a second optical path generally counterdirectional to the first optical path and sharing a common optical axis with the first optical path for at least a portion of the first and second optical paths, the second optical path passing from the target skin area through the cooling window, engaging the at least one second optical element, and being reflected by the first mirror onto the temperature sensing element;
   g) determining the surface temperature of the target skin area one or more times before, during, or after the application of the at least one therapeutic laser pulse to the target skin area based on the infrared energy sensed by the temperature sensing element.

202. The method of paragraph 201, wherein the skin contact element is a contact cooling element.

203. The method of paragraph 202, wherein contacting the first skin area comprises contacting the first skin area with the cooling window.

204. The method of paragraph 203, further comprising:
   h) cooling the first skin area from a first temperature to a second temperature using the cooling window.

205. The method of paragraph 204, further comprising
   i) performing at least one responsive action based on the surface temperature of the target skin area, the responsive action selected from:
      1) terminating the application of the at least one therapeutic laser pulse to the target skin area based on the determined surface temperature;
      2) indicating the instantaneous surface temperature of the target skin area;
      3) indicating a maximum surface temperature of the target skin area;
      4) changing at least one parameter of the laser therapy; and
      5) indicating when the surface temperature of the target skin area returns to a desired temperature following delivery of one or more therapeutic laser pulses to the target skin area.

The particular embodiments disclosed and discussed above are illustrative only, as the invention may be modified and practiced in different but equivalent manners apparent to those skilled in the art having the benefit of the teachings herein. Embodiments of the present invention disclosed and claimed herein may be made and executed without undue experimentation with the benefit of the present disclosure. While the invention has been described in terms of particular embodiments, it will be apparent to those of skill in the art that variations may be applied to systems and apparatus described herein without departing from the concept and scope of the invention. Examples are all intended to be non-limiting. It is therefore evident that the particular embodiments disclosed above may be altered or modified and all such variations are considered within the scope of the invention, which are limited only by the scope of the claims.

What is claimed is:

1. A method for treating the skin of a patient with one or more therapeutic laser pulses, the method comprising:
   a) using a laser source for generating therapeutic laser pulses for application to a plurality of target skin areas as a laser therapy;
   b) using a handpiece optically coupled to the laser source to receive the therapeutic laser pulses from the laser source and direct each therapeutic laser pulse to one of the plurality of target skin areas along a first optical path, wherein at least a portion of the first optical path is different for each target skin area of the plurality of target skin areas, the handpiece comprising:
      1) a first optical element comprising a reflective element and having a reflective portion and a first open area comprising one of an aperture and a slot, wherein the first open area is located in the first optical path for each target skin area of the plurality of target skin areas;
      2) at least a second optical element comprising a movable mirror that is movable to a plurality of different mirror positions, wherein the movable mirror is located in the first optical path for each target skin area of the plurality of target skin areas;
      3) a contact cooling unit comprising a cooling window adapted to contact and cool a first skin area of the patient, wherein the cooling window comprises a thermally conductive material that is located in the first optical path for each target skin area of the plurality of target skin areas and is transmissive to infrared energy and the therapeutic laser pulses, and wherein each target skin area of the plurality of target skin areas comprises a different fraction of the first skin area cooled by the contact cooling window; and
      4) a temperature sensing element for sensing, at each of the plurality of different mirror positions, infrared energy radiated from substantially only a selected one of the plurality of target skin areas through the cooling window along a second optical path that is generally counterdirectional to, and shares a common optical axis with, the first optical path for the selected one of the plurality of target skin areas, wherein
         A) at least a portion of the second optical path for each target skin area of the plurality of target skin areas is different from every other second optical path;
         B) the movable mirror and the reflective portion of the first optical element are located in the second optical path for each target skin area of the plurality of target skin areas;
         C) the movable mirror is positioned within the handpiece to, at each of the plurality of different positions, direct one or more laser pulses to the selected one of the plurality of target skin areas along the first optical path, receive infrared energy radiated along the second optical path from substantially only the selected one of the plurality of target skin areas through the cooling window, and direct at least a portion of the received infrared energy to the reflective portion of the first optical element;
         D) the reflective portion of the first optical element is positioned to receive the at least a portion of the infrared energy from the movable mirror and to reflect the infrared energy received from the movable mirror to the temperature sensing element; and
         E) the temperature sensing element is adapted to generate a first signal indicative of the infrared energy received from the first optical element;
   c) using a temperature determination unit adapted to determine a surface temperature of the selected one of the plurality of target skin areas based on the infrared energy received from the first optical element, the temperature determination unit comprising a controller comprising at least one processor adapted to process the first signal to determine the surface temperature of the selected one of the plurality of target skin areas at one or more timepoints before, during, or after the application of one or more of the therapeutic laser pulses to the selected one of the plurality of target skin areas;
   d) contacting the first skin area with the cooling window;
   e) cooling the first skin area from a first temperature to a second temperature using the cooling window;
   f) generating at least one first therapeutic laser pulse using the laser source;
   g) receiving the at least one first therapeutic laser pulse from the laser source with the handpiece;
   h) applying the at least one first therapeutic laser pulse to a selected one of the plurality of target skin areas, the at least one first therapeutic laser pulse passing through the first open area, engaging the at least a second optical element, and passing through the cooling window along the first optical path for the selected one of the plurality of target skin areas;
   i) determining the surface temperature of the selected one of the plurality of target skin areas one or more times before, during or after the application of the at least one first therapeutic laser pulse using the temperature determination unit;
   j) performing at least one responsive action in response to determining the surface temperature of the selected one of the plurality of target skin areas, selected from
      1) terminating the application of the at least one first therapeutic laser pulse to the selected one of the plurality of target skin areas based on the determined surface temperature;
      2) indicating the instantaneous surface temperature of the selected one of the plurality of target skin areas;
      3) indicating a maximum surface temperature of the target skin area;
      4) changing at least one parameter of the laser therapy; and
      5) indicating when the surface temperature of the selected one of the plurality of target skin areas returns to a desired temperature following delivery of the at least one therapeutic laser pulse.

2. The method of claim 1, wherein determining the surface temperature of the selected one of the plurality of target skin areas comprises determining the surface temperature of the selected one of the plurality of target skin areas a plurality of times before, during, or after the application of the at least one therapeutic laser pulse.

3. The method of claim 1, wherein determining the surface temperature of the selected one of the plurality of target skin areas comprises determining the surface temperature at least a first time during the application of the at least one therapeutic laser pulse and at least a second time before or after the application of the at least one therapeutic laser pulse.

4. The method of claim 1, wherein using a handpiece comprising a movable mirror comprises using a handpiece comprising a mirror movable in at least two axes to direct at least one therapeutic laser pulse to each of a plurality of target skin areas within the first skin area.

5. The method of claim 4, wherein applying at least one therapeutic laser pulse to a selected one of the plurality of target skin areas comprises applying at least one first therapeutic laser pulse to a first target skin area with the mirror in a first position to direct at least one first therapeutic laser pulse to the first target skin area, the method further comprising, after steps (f)-(i):
k) moving the mirror to a second position to direct at least one second therapeutic laser pulse to a second target skin area different from the first target skin area;
l) generating at least one second therapeutic laser pulse using the laser source;
m) receiving the at least one second therapeutic laser pulse from the laser source with the handpiece;
n) applying the at least one second therapeutic laser pulse to the second target skin area; and
o) determining the surface temperature of the second target skin area one or more times before, during or after the application of the at least one second therapeutic laser pulse using the temperature determination unit.

6. The method of claim 5, wherein determining the surface temperature of the second target skin area comprises determining the surface temperature of the second target skin area a plurality of time times before, during, or after the application of the at least one second therapeutic laser pulse.

7. The method of claim 1, wherein determining the surface temperature of the selected one of the plurality of target skin areas comprises determining the surface temperature of the selected one of the plurality of target skin areas at a temperature determination rate of 10-1,000,000 times per second.

8. The method of claim 1, wherein determining the surface temperature of the selected one of the plurality of target skin areas comprises determining the surface temperature of the selected one of the plurality of target skin areas at a temperature sampling time interval of 100 msec or less.

9. The method of claim 1, wherein using a handpiece comprising at least a second optical element comprises using a handpiece having a plurality of lenses and the movable mirror, and at least two of the plurality of lenses and the second mirror are located in the first optical path and the second optical path for each target skin area of the plurality of target skin areas.

10. The method of claim 1, wherein providing a handpiece comprising at least a second optical element comprises providing a handpiece having at least four lenses and at least one mirror.

11. The method of claim 1, further comprising repeating steps (f)-(h) to generate and apply therapeutic laser pulses to the selected one of the plurality of target skin areas until the determined surface temperature of the selected one of the plurality of target skin areas reaches a target treatment temperature.

12. The method of claim 1, wherein determining the surface temperature of the selected one of the plurality of target skin areas one or more times comprises repeatedly determining the surface temperature of the target skin area a plurality of times during the application of a single therapeutic laser pulse, the method further comprising terminating the application of the single therapeutic laser pulse when the surface temperature of the target skin area reaches a target treatment temperature.

* * * * *